(12) United States Patent
Ganguly et al.

(10) Patent No.: US 12,213,819 B2
(45) Date of Patent: Feb. 4, 2025

(54) MULTI-MAXIMUM X-RAY SPECTRUM SYSTEMS AND MULTI-LAYER IMAGING SYSTEMS

(71) Applicant: Varex Imaging Corporation, Salt Lake City, UT (US)

(72) Inventors: Arundhuti Ganguly, San Jose, CA (US); Ivan P. Mollov, San Jose, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 0 days.

(21) Appl. No.: 18/487,418

(22) Filed: Oct. 16, 2023

(65) Prior Publication Data

US 2024/0057953 A1 Feb. 22, 2024

Related U.S. Application Data

(63) Continuation of application No. 16/836,735, filed on Mar. 31, 2020, now Pat. No. 11,819,348.

(60) Provisional application No. 62/977,033, filed on Feb. 14, 2020.

(51) Int. Cl.
| | |
|---|---|
| *G01T 1/00* | (2006.01) |
| *A61B 6/00* | (2024.01) |
| *A61B 6/40* | (2024.01) |
| *G01T 1/20* | (2006.01) |
| *G01T 1/34* | (2006.01) |

(52) U.S. Cl.
CPC .......... *A61B 6/4042* (2013.01); *A61B 6/4035* (2013.01); *A61B 6/482* (2013.01); *G01T 1/2006* (2013.01); *G01T 1/2014* (2013.01); *G01T 1/34* (2013.01)

(58) Field of Classification Search
CPC ..................................................... G01T 1/242
See application file for complete search history.

(56) References Cited

U.S. PATENT DOCUMENTS

| | | | |
|---|---|---|---|
| 5,138,167 A | 8/1992 | Barnes | |
| 5,285,489 A | 2/1994 | Ohtsuchi et al. | |
| 5,365,567 A | 11/1994 | Ohtsuchi et al. | |
| 6,285,740 B1 | 9/2001 | Seely et al. | |
| 7,569,832 B2 | 8/2009 | Tredwell et al. | |
| 7,573,040 B2 | 8/2009 | Tkaczyk et al. | |
| 7,613,274 B2 | 11/2009 | Tkaczyk et al. | |
| 7,834,321 B2 | 11/2010 | Yorkston | |
| 8,440,978 B2 | 5/2013 | Morf | |
| 2011/0058649 A1* | 3/2011 | Wear | A61B 6/505 257/E31.015 |
| 2012/0189102 A1* | 7/2012 | Maurer, Jr. | A61N 5/1081 378/65 |
| 2021/0041582 A1* | 2/2021 | Simon | G01T 1/2018 |

* cited by examiner

*Primary Examiner* — Dani Fox

(74) *Attorney, Agent, or Firm* — Laurence & Phillips IP Law

(57) ABSTRACT

Some embodiments include an x-ray system, comprising: a housing; a plurality of overlapping imaging layers disposed in the housing, each imaging layer configured to generate an image in response to a corresponding incident x-ray beam; and a plurality of x-ray markers attached to the housing and disposed to affect the incident x-ray beam for each of the imaging layers.

18 Claims, 19 Drawing Sheets

MULTI-MAXIMUM X-RAY SPECTRUM SYSTEMS AND MULTI-LAYER IMAGING SYSTEMS

Multiple layer imaging systems have been used to provide energy discrimination in an incident x-ray beam. Using multiple layers may increase absorption and overall detected quantum efficiency (DQE). Multiple layer imagers may be operated without a special purpose, dual energy x-ray generator. The multiple layers may reduce mis-registration as the layers may be exposed at the same time.

DETAILED DESCRIPTION

Some embodiments relate to multi-maximum x-ray spectrum systems and multi-layer imaging systems. Different materials have different x-ray absorption of x-rays. X-ray sources may produce a wide spectrum of x-rays which are absorbed differently by different parts or materials of the body or object. In some embodiments, image layers may be cascaded, i.e., one disposed behind the other relative to an incoming x-ray beam. The imaging layer closer to the x-ray source may absorb the lower energy x-rays passing through the body/object. Each imaging layer may act as an x-ray filter for the next imaging layer or layers. Scintillator and direct x-ray conversion materials, used in each of the imaging layers, can be chosen to optimize the intended x-ray spectrum to be absorbed in the respective layer, chosen depending on the particular application, or the like. The images from the multiple imaging layers may be combined through spatial scaling, registration, and other math operations (e.g., subtraction) to create an image with better contrast for a specific material.

However, while the multiple layers alone can improve energy discrimination, the improvement may not be adequate as the average energies of the x-rays absorbed in each of the layers may not be far apart. X-ray filters may be used between the imaging layers to improve energy discrimination; however, that may lead to a loss of x-rays, reducing DQE and/or increasing the required dose.

Some embodiments may adjust the spectrum of the x-ray beam before it is incident on a patient or object. For example, the spectrum of the x-ray beam may be adjusted to have an energy spectrum with multiple local maximums.

Figure 1:
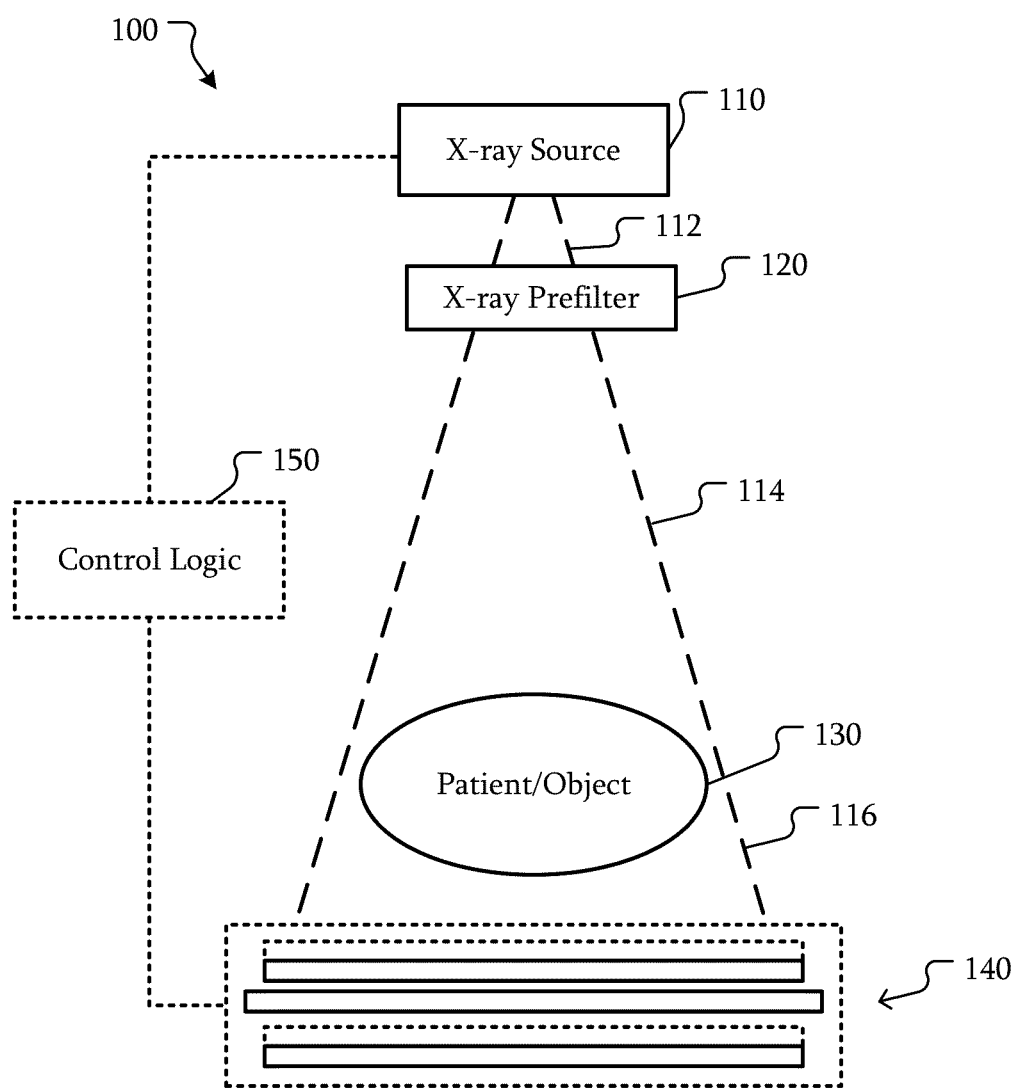
FIG. 1 is a block diagram of an x-ray system according to some embodiments.

FIG. 1 is a block diagram of an x-ray system according to some embodiments. The x-ray system 100 includes an x-ray source 110, an x-ray prefilter 120. The x-ray source 110 is configured to generate an x-ray beam 112. The x-ray source 110 may include an x-ray tube, a linear accelerator, or the like.

In some embodiments, the x-ray system 100 includes an x-ray imager 140 including multiple imaging layers. Each of the imaging layers is configured to generate a separate image. The imaging layers each include an x-ray conversion material, scintillator, direct conversion material or the like. For example, an x-ray conversion material may include gadolinium oxysulfide ($Gd_2O_2S$; GOS; Gadox), gadolinium oxysulfide doped with terbium ($Gd_2O_2S$:Tb), cesium iodide (CsI), or the like. Although some materials of the scintillator have been used as examples, in other embodiments, the material may be different depending on the particular system 100.

Figure 2A:
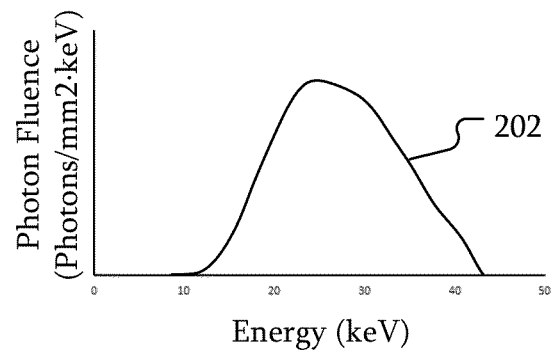
FIGS. 2A and 2B are charts of energy spectrums with and without a prefilter according to some embodiments.
Figure 2B:
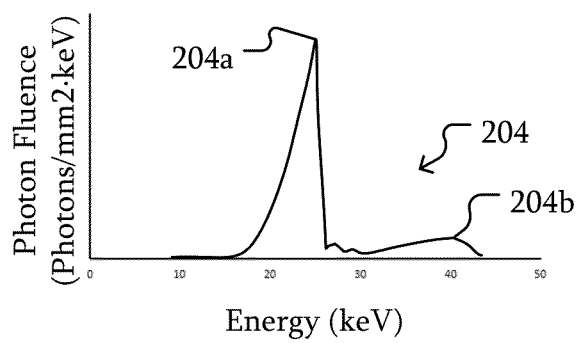

The x-ray prefilter 120 is a material and/or structure configured to change a spectrum of the x-ray beam 112. In an embodiment, the energy spectrum is an x-ray or x-radiation spectrum from 0.1 kiloelectron volt (keV) to 200 keV. As will be described in further detail below, in some embodiments, the x-ray prefilter 120 may be configured to transform an energy spectrum with one local maximum in the range of interest, (as illustrated in FIG. 2A), into a spectrum with at least one local minimum between two or more local maximums in the range of interest. A local maximum is a portion of the x-ray energy spectrum for which the x-ray flux is greater than the x-ray flux for energies immediately lower or immediately higher. An example of such a spectrum with multiple local maximums may include a spectrum with a first local maximum at about 23 keV and a second local maximum at about 40 keV (as illustrated in FIG. 2B); however, the number of local maximums and the values may be different in other embodiments. The local minimum may be located between 23 and 40 keV, such as at about 24 keV. In an example, the local maximum and the local minimum can be represented as photon fluence per unit of energy using units such as photons/$mm^2 \cdot keV$. Fluence or radiant exposure is the radiant energy received by a surface per unit area. Photon fluence is the number of photons that cross a unit area. In an example, the local minimum may be at least 50% less than one or more adjacent local maximums.

The depth of the local minimum relative to the adjacent local maximums may be different depending on the x-ray prefilter 120. For example, the x-ray prefilter may have an attenuation coefficient peak of about 100 $cm^{-1}$ at an energy of interest such as about 24 keV while at slightly lower energies of about 23 keV, the x-ray prefilter may have an attenuation coefficient of about 25 cm$^{-1}$. Thus, a resulting local minimum at about 24 keV may be lower than a local maximum at about 23 keV by a factor of 4. The relative difference between the local minimum and other local maximums may be different. Although a factor of 4 has been used as an example, the relative difference may be different. In an embodiment, the local minimum may be lower than the local maximum by a factor of at least 2. In another embodiment, the energy of the local minimum may be within 5%, 10%, or 15% of the energy of one of the local maximums. For example, if a local maximum is at about 23 keV, then the local minimum may be between 21.85 keV and 24.15 keV for 5%, between 20.7 keV and 25.3 keV for 10%, and between 19.55 keV and 26.45 keV for 15%. In an embodiment, the local maximum differs from each other in energy by at least 10%, 15%, 20%, or 25% of the average energy of at least two local maximums. For example, if the first local maximum is at about 23 keV and the second local maximum is at about 40 keV, the average is 31.5 keV ((23+40)/2 keV) and 10%, 15%, 20%, or 25% of the average is 3.15 keV, 4.725 keV, 6.3 keV, and 7.875 keV, respectively. In another embodiment, the local maximum differs from each other by at least at least 4 keV.

The range of interest within the x-ray energy spectrum may differ based on the imaging application. For example, the range of interest in mammography applications may be between 10 keV to 50 keV, which can be called the mammography spectrum. In another example, the range of interest in radiography applications may be between 30 keV to 100 keV, which can be called the radiography spectrum. While the mammography spectrum and radiography spectrum are used as examples, other ranges of interest may also be used.

FIGS. 2A and 2B are charts of energy spectrums with and without a prefilter according to some embodiments. For FIGS. 2A-4B and 8-9, the x-axis represents the energy measured in keV and the y-axis represents the energy-dependent photon fluence or photon fluence per unit of energy measured in photons/mm$^2$·keV. Referring to FIGS. 1 and 2A, the spectrum 202 may represent the spectrum of the x-ray beam 112. This spectrum 202 may already include some filtering such as filtering to reduce lower energy components. However, the spectrum 202 has a single local maximum.

Referring to FIGS. 1 and 2B, the spectrum 204 represents the filtered x-ray beam 114 after the x-ray beam 112 has passed through the x-ray prefilter 120. The x-ray prefilter 120 may include one or more materials having k-edges. In x-ray absorption spectroscopy (XAS), the k-edge is a sudden increase in x-ray absorption occurring when the energy of the x-rays is just above the binding energy of the innermost electron shell of the atoms interacting with the photons. The term "k-edge" is based on x-ray notation, where the innermost electron shell is known as the k-shell. Examples of such materials having k-edges include palladium, rhodium, silver, cadmium, indium, tin, antimony, or any element having an atomic number from 37 (rubidium) to 92 (uranium); or composites of these elements including oxides, nitrides, and sulfides; combinations or mixtures of such materials, or the like. In this example, the x-ray prefilter 120 includes three materials having different k-edges at energies between about 25 keV and about 30 keV. The combination of those materials filters the spectrum 202 to generate the bimodal spectrum 204 including a first local maximum 204a and a second local maximum 204b.

When one or more materials with k-edges are used, the resulting spectrum may have two or more local maximums where the k-edge of the one or more materials is between the resulting local maximums of the spectrum 204. In some embodiments, each of the materials has a different k-edge energy.

In some embodiments, the materials may be selected such that the k-edges occur between the desired local maximums of the spectrum. That is the k-edge(s) form a band-stop filter at and slightly above the k-edge(s). For example, the x-ray prefilter 120 may have materials with k-edges at about 26, 28, and 30 keV. The combination of these materials results in a greater absorption at or slightly above those energies. In particular, the sharp drop of the first local maximum 204a is due to the lowest k-edge material. The other materials may be used to further shape the energies and/or to reduce the higher energy local maximum 204b to a desired level.

In some embodiments, the x-ray prefilter 120 includes a pure form of an element. In other embodiments, the x-ray prefilter 120 includes an alloy of such materials. In other embodiments, the x-ray prefilter 120 includes a powdered form of one or more such materials. In other embodiments, the x-ray prefilter 120 includes multiple sheets of such materials. For example, the materials may be formed into a sheet having a thickness of about 50 μm. In other embodiments, the thickness of the sheet may be about 5 μm to about 20 millimeter (mm). Sheets of different materials may be stacked to form the x-ray prefilter 120.

Figure 3A:
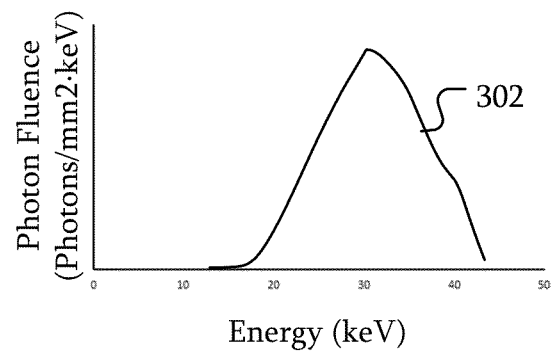
FIGS. 3A and 3B are charts of energy spectrums at an imager with and without a prefilter according to some embodiments.
Figure 3B:
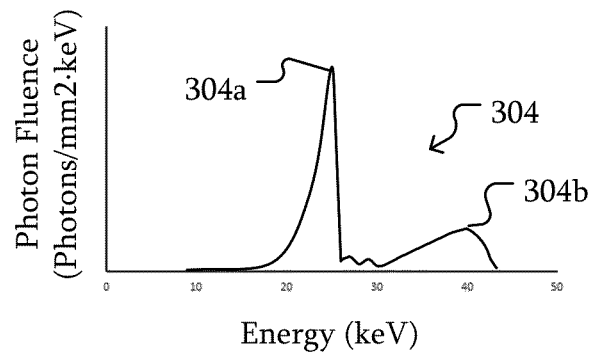

FIGS. 3A and 3B are charts of energy spectrums at an imager with and without a prefilter according to some embodiments. Referring to FIGS. 1 and 3A, the spectrum 302 is an example of a spectrum of the x-ray beam 116 after a patient 130 and at an entrance of an x-ray imager 140 where the spectrum of the incident x-ray beam 114 on the patient 130 was spectrum 202, without an x-ray prefilter 120.

Referring to FIGS. 1 and 3B, the spectrum 304 is an example of a spectrum of the x-ray beam 116 after a patient 130 and at an entrance of the x-ray imager 140 where the spectrum of the incident x-ray beam 114 on the patient was spectrum 204 where the x-ray prefilter 120 was used. The lower energy local maximum 304a and the higher energy local maximum 304b correspond to the lower energy local maximum 204a and the higher energy local maximum 204b of FIG. 2B. The lower energy local maximum 304a may be reduced more than the higher energy local maximum 304b as more of the lower energy photons may be absorbed by the patient 130. As a result, the intensity difference between the peaks 304a and 304b may be reduced.

Figure 4A:
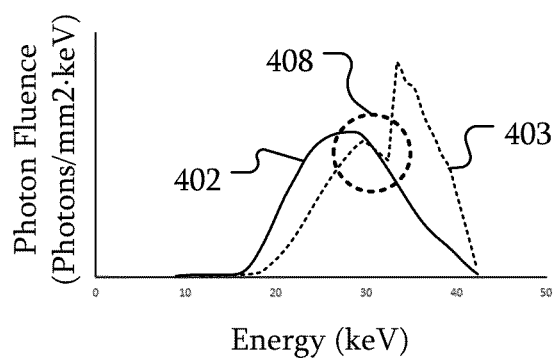
FIGS. 4A and 4B are charts of energy spectrums of x-rays absorbed in two scintillators of an imager with and without a prefilter according to some embodiments.
Figure 4B:
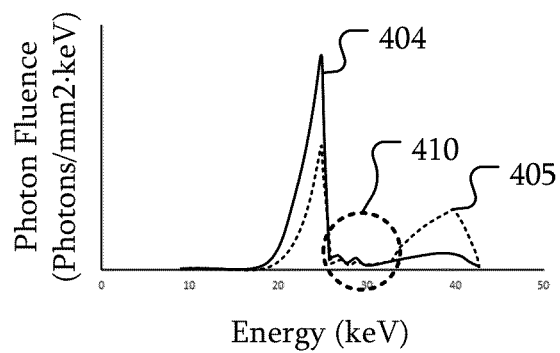

FIGS. 4A and 4B are charts of energy spectrums of x-rays absorbed by two scintillators of an imager with and without a prefilter according to some embodiments. Referring to FIGS. 1 and 4A, the spectrums 402 and 403 represent the spectrum of the x-rays absorbed in scintillators of different layers of the x-ray imager 140 where the x-ray prefilter 120 was not used. Spectrum 402 is the spectrum absorbed in the first scintillator. Spectrum 403 is the spectrum absorbed in the second scintillator, which is different than the first scintillator. In some embodiments, the first scintillator is configured to convert x-rays more efficiently in a range of energies lower than that of the second scintillator. In other embodiments, the first and second scintillators may include the same type, material, or the like and may have substantially the same properties. In some embodiments, the spectrum 403 may be reduced before entering the second scintillator due to the beam passing through the first scintillator of the associated layer of the x-ray imager 140.

An image may be generated at least in part by subtracting or performing other operations on the output images of the two layers of the x-ray imager 140. The spectrums 402 and 403 overlap significantly, in region 408. As a result, the contributions of the two layers may cancel each other out, resulting in little to no information. However, the patient still received a dose for that energy range of photons without a corresponding benefit in image contrast or image information.

In contrast, referring to FIGS. 1 and 4B, in some embodiments, the spectrums 404 and 405 again represent the spectrum absorbed in a first scintillator and the spectrum absorbed in a second scintillator, respectively. In some embodiments, the scintillators and imaging layers may be identical to those that resulted in the spectrums 402 and 403. However, because the spectrum of the x-ray beam 112 had been shaped by the x-ray prefilter 120, a region 410 where the absorbed energies are similar in both imaging layers is substantially reduced. As a result, the patient received less dose for energies that would contribute little to no imaging information.

In some embodiments, the x-ray prefilter 120, the x-ray conversion materials of the layers of the imager 140, or the like may be selected to maximize the difference between the spectrums of the absorbed x-rays 404 and 405 in multiple energy ranges. For example, the selection may result in the amount of absorbed x-rays corresponding to the spectrum 404 being higher than the amount of absorbed x-rays corresponding to the spectrum 405 in a first energy range, such as from about 15 keV to about 25 keV, while the amount of absorbed x-rays corresponding to the spectrum 404 is lower than the amount of absorbed x-rays corresponding to the spectrum 405 in a second, different energy range, such as from about 30 keV to about 45 keV. That is, in the first energy range, the net transfer function from the x-ray source 110 to the imaging layer resulting in the amount of absorbed x-rays corresponding to spectrum 404 may be greater than the net transfer function from the x-ray source 110 to the imaging layer resulting in the amount of absorbed x-rays corresponding to spectrum 405. In contrast, in the second energy range, the net transfer function from the x-ray source 110 to the imaging layer resulting in the amount of absorbed x-rays corresponding to spectrum 404 may be less than the net transfer function from the x-ray source 110 to the imaging layer resulting in the amount of absorbed x-rays corresponding to spectrum 405. As a result, lower energy x-rays result in a larger signal in a first imaging layer than a second imaging layer while higher energy x-rays result in a larger signal in the second imaging layer than the first imaging layer.

Referring to FIG. 1, in some embodiments, an anode of the x-ray source 110 includes at least two materials corresponding to the local maximums of the multi-maximum spectrum. For example, materials for the anode may include tungsten (W), molybdenum (Mo), rhodium (Rh), silver (Ag), rhenium (Re), palladium (Pd), or the like. In some embodiments, the materials may be selected based on specific k-peaks in the associated x-ray spectrum. Although an x-ray source 110 that may generate an x-ray beam 112 having a multi-maximum energy distribution, in other embodiments, the x-ray filter 120 may transform the single-maximum energy distribution into the multi-maximum energy distribution. That is, the x-ray source 110 may, but need not be a dual or multiple energy x-ray source.

In some embodiments, the x-ray system 100 includes control logic 150 configured to combine images from the imaging layers into a combined image. The control logic 150 may include a general purpose processor, a digital signal processor (DSP), an application specific integrated circuit, a microcontroller, a programmable logic device, discrete circuits, a combination of such devices, or the like. The control logic 150 may include internal portions, such as registers, cache memory, processing cores, or the like, and may also include external interfaces, such as address and data bus interfaces, interrupt interfaces, or the like. In addition, the control logic 150 may include interface devices, such as logic chipsets, hubs, memory controllers, communication interfaces, or the like may be part of the system 100 to connect the processor 102 to internal and external components. The combination of the images may be performed using a variety of operations such as subtraction, multiplication, division, addition, non-linear operations, or the like.

Figure 5:
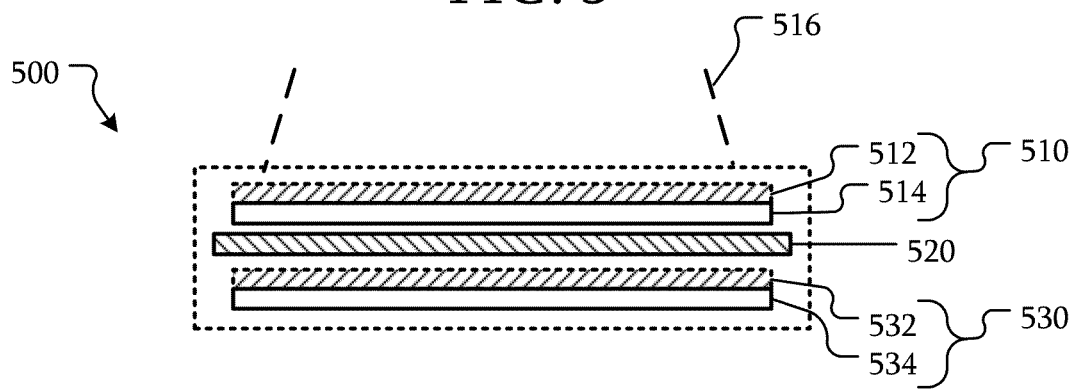
FIG. 5 is a block diagram of an imager of the system of FIG. 1 according to some embodiments.

FIG. 5 is a block diagram of an example of an imager 140 of the system of FIG. 1 according to some embodiments. Referring to FIGS. 1 and 5, the imager 500 includes multiple imaging layers. Here, imaging layers 510 and 530 are used as examples; however, in other embodiments more than two imaging layers may be present.

In some embodiments, the imaging layers 510 and 530 are separated by an x-ray filter 520. The x-ray filter 520 may be configured to adjust the spectrum of the x-ray beam incident on the imaging layer 530. For example, the imaging layer 530 may be used to detect higher energy x-rays. The x-ray filter 520 may attenuate lower energy x-rays more than higher energy x-rays. In some embodiments, the x-ray filter 520 may include a k-edge material. The material may be selected to have a k-edge lower than that of the x-ray conversion material of the scintillator 532. As a result, more lower energy x-ray photons may be absorbed in the x-ray filter 520 instead of being converted in the scintillator 532. For example, the x-ray filter 520 may include a material that has a k-edge at an energy lower than an energy range of interest for the particular application. In a particular example, if a working energy range is 10 keV to 50 keV such as in a mammography application, a material such as copper, nickel, or the like may be used, which has a k-edge lower than 10 keV. In another example, with a working energy range of 30 keV to 100 keV such as in radiography, a different material may be selected that has a k-edge lower than 30 keV, such as palladium, rhodium, or the like. Such a material may further reduce the lower energy part of the x-rays that pass through the imaging layer 510.

Each imaging layer may include an x-ray conversion material and a sensor array. Here, imaging layer 510 includes scintillator 512 and sensor array 514 and imaging layer 530 includes scintillator 532 and sensor array 534. While imaging layers have been described as including scintillators, in other embodiments, one or more of the imaging layers may include direct conversion sensors to directly convert the x-ray photons into a signal without converting the x-ray photons into other photons before detection. Thus, direct conversion imaging layers 510 and 530 each may include just a sensor array 514 or 534, respectively. For example, the direct conversion sensors may include cadmium telluride (CdTe), cadmium zinc telluride (CdZnTe or CZT), selenium, or the like.

X-ray beam 516 may be incident on the imager 500 after passing through a patient. The first imaging layer 510 is disposed to receive the x-ray beam 516 before the second imaging layer 530.

As described above, the incident x-ray beam 516 may have a multi-maximum energy spectrum. In some embodiments, the imaging layers may each be associated with a different part of the spectrum. For example, the scintillator 512 of the first imaging layer 510 may be configured to absorb more of a lower energy part of the spectrum than the scintillator 532 while the scintillator 532 may be configured to absorb more of a higher energy part of the spectrum than the scintillator 512. In some embodiments, each of the imaging layers include an x-ray conversion material associated with a corresponding one of the local maximums of the multi-maximum spectrum.

In some embodiments, the x-ray conversion materials of the scintillators 512 and 532 may be different. In other embodiments, the x-ray conversion materials may be the same. In still other embodiments, some of the x-ray conversion materials of some imaging layers may be the same while others may be different.

In some embodiments, a thickness of the scintillators 512 and 532 may be different. The thickness may be selected to optimize the conversion of the x-ray photons in an energy range associated with that imaging layer 510 or 530.

Figure 6A:
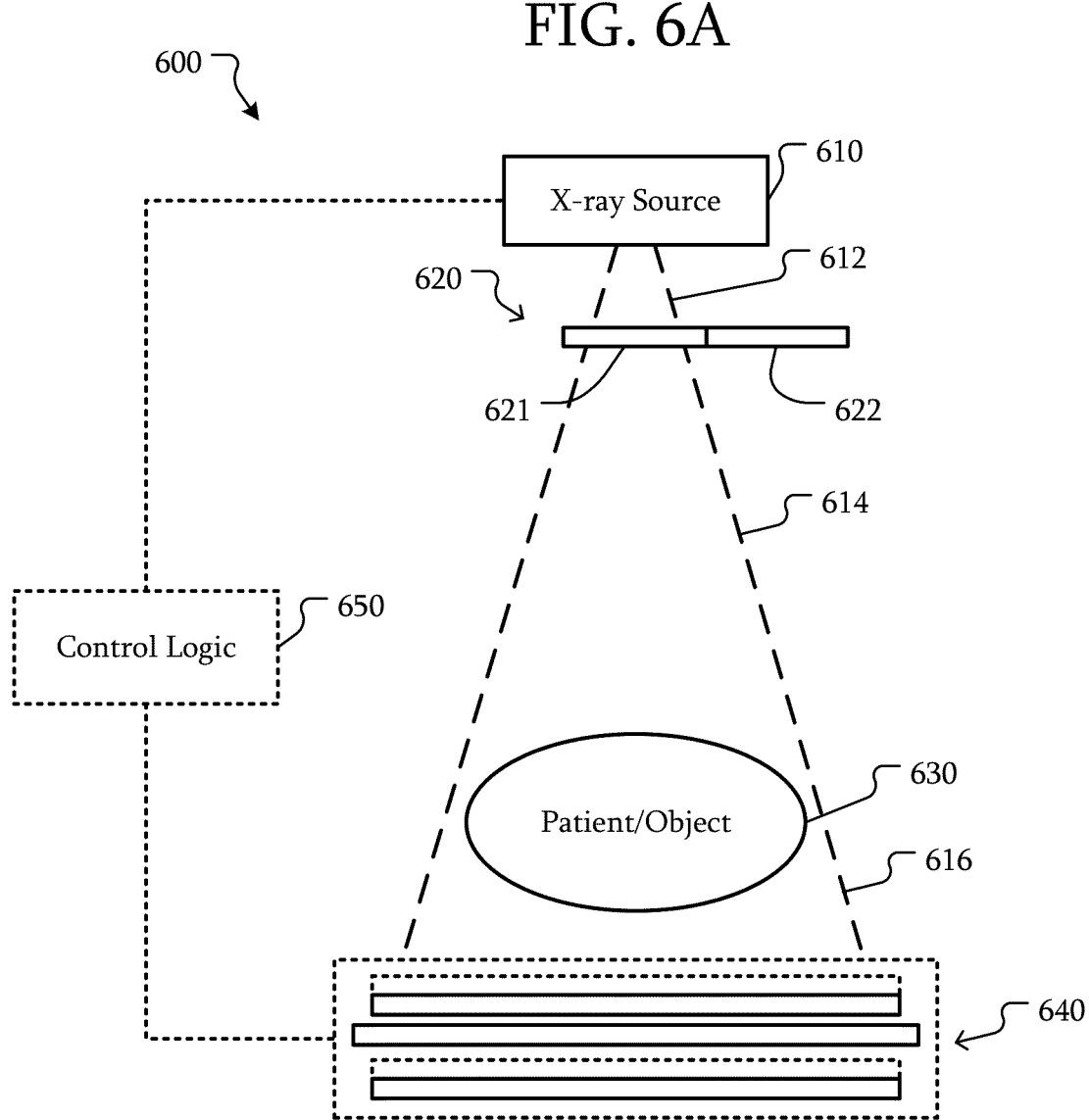
FIGS. 6A and 6B are block diagrams of an x-ray system according to some embodiments.
Figure 6B:
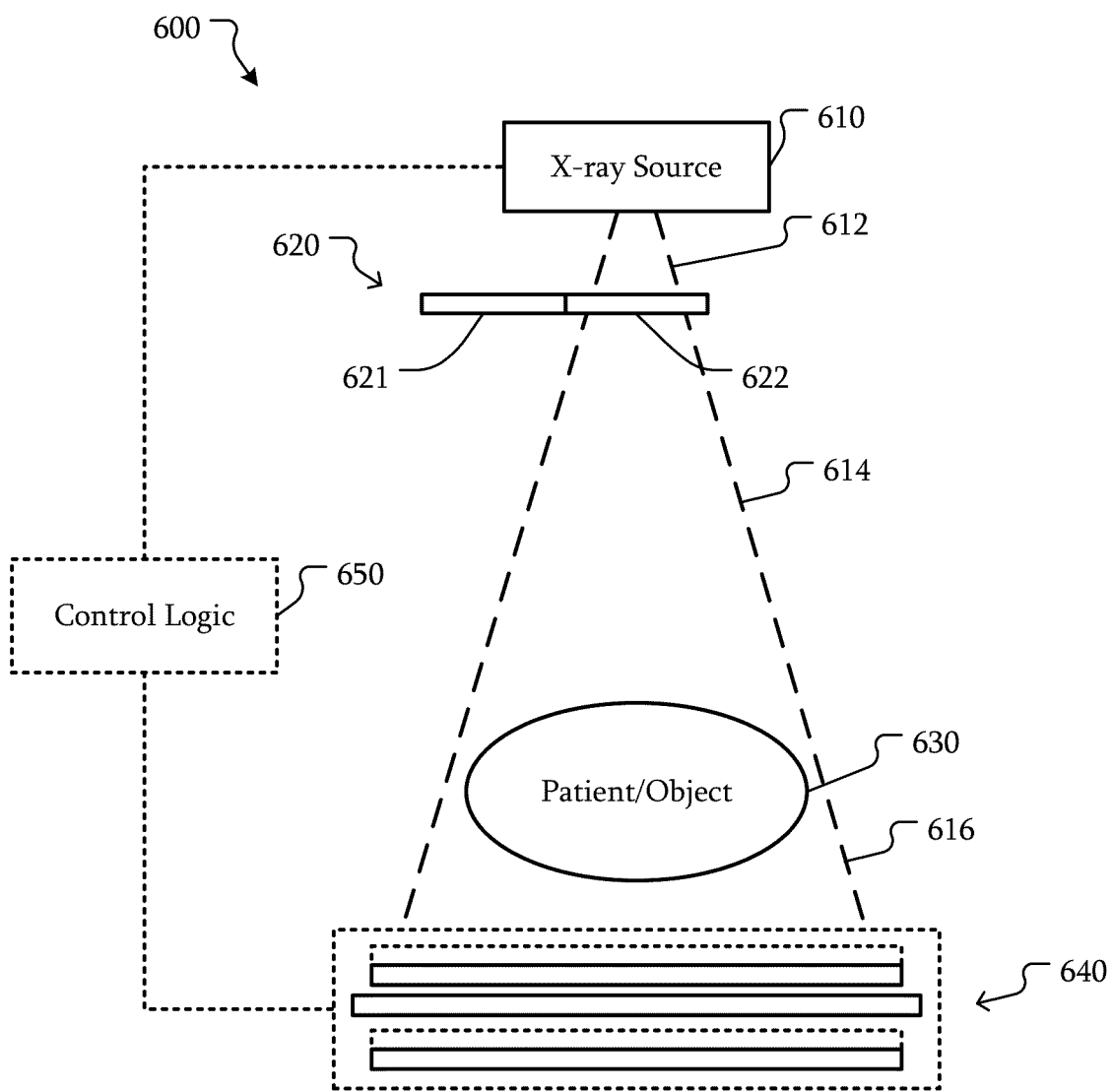

FIGS. 6A and 6B are block diagrams of an x-ray system according to some embodiments. Referring to FIGS. 6A and 6B, the x-ray system 600 includes an x-ray source 610 and a movable x-ray prefilter 620. The x-ray source 610 may be similar to the x-ray source 110 described above and may be configured to generate the x-ray beam 612.

The movable x-ray prefilter 620 may be similar to the x-ray prefilter 120 described above, including similar materials. However, the movable x-ray prefilter 620 includes multiple filter regions. Each of the regions may have at least partially different materials similar to the x-ray prefilter 120. Here, two filter regions 621 and 622 are used as examples; however, in other embodiments, the movable x-ray prefilter 620 may include more regions.

Of the multiple filter regions, at least one of the filter regions has an attenuation characteristic that is different from at least one of the other filter regions. In an embodiment, the attenuation characteristic includes an attenuation coefficient. Here, the attenuation characteristics of region 621 is different from that of region 622. In some embodiments, the filter region 621 is configured such that the x-ray beam 614 has a first energy peak when filtered by the filter region 621 and the second filter region 622 is configured such that the x-ray beam 614 has a second energy peak when filtered by the second filter region 622. An energy of the first energy peak may be different than an energy of the second energy peak. One or more of the regions of the x-ray prefilter 620 may include a material with a k-edge as described above with respect to x-ray filter 120. However, in other embodiments, one or more of the regions of the x-ray prefilter 620 may not have materials with such a k-edge.

The x-ray prefilter 620 is movable. In FIG. 6A, the x-ray prefilter 620 has been moved to be in a position where the x-ray beam 612 passes through region 621. In FIG. 6B, the x-ray prefilter 620 has been moved to be in a position where the x-ray beam 612 passes through region 622.

In some embodiments, the system 600 may include an imager 640. The imager 640 may be similar to the imager 140 described above. The x-ray prefilter 620 may be moved such that during an exposure of the imager 640, the state of the x-ray prefilter 620 may be changed.

In some embodiments, the system 600 includes control logic 650. The control logic 650 may be similar to the control logic 150 described above. The control logic 650 may be configured to control a position of the movable x-ray prefilter 620. However, in some embodiments, the control logic 650 may not control a position of the x-ray prefilter 620. For example, the x-ray prefilter 620 may be continuously moving to switch the region that is currently in the path of the x-ray beam 612.

In some embodiments, the control logic 650 may be configured to monitor a position of the x-ray prefilter 620. In response to the monitored position, the control logic 650 may be configured to adjust the operation of the x-ray source 610, such as turning it on and off, changing the power, or the like based on the position.

In some embodiments, the control logic 650 may be configured to synchronize the position of the x-ray prefilter 620 with at least one of the x-ray source 610 operation and the acquisition of an image by one or more imaging layers of the imager 640. For example, the control logic 650 may be configured to turn on the x-ray source 610 and enable an acquisition of the imaging layers of the imager 640.

Figure 7A:
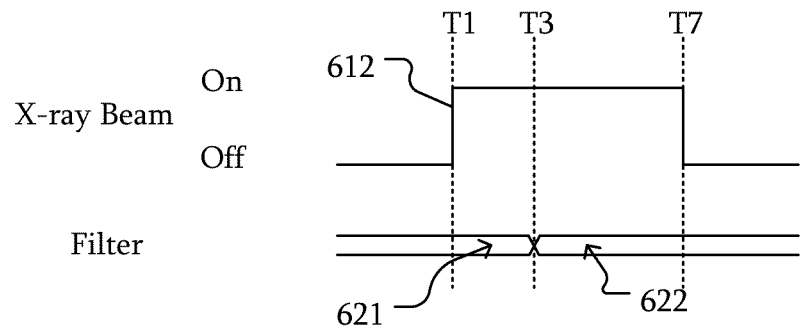
FIGS. 7A-7D are timing diagrams illustrating a position of an x-ray prefilter and a state of an x-ray beam according to some embodiments.

FIGS. 7A-7D are timing diagrams illustrating a position of a movable x-ray prefilter 620 and a state of an x-ray beam 612 according to some embodiments. Referring to FIGS. 6A, 6B, and 7A, in some embodiments, region 621 of the x-ray prefilter 620 may be moved to be in the path of the x-ray beam 612. The x-ray beam 612 may be turned on at time T1. As a result, the filtered x-ray beam 614 may be filtered according to region 621 from time T1 to time T3.

At time T3, the x-ray prefilter 620 may be moved so that region 622 is in the path of the x-ray beam 612, resulting in a filtered x-ray beam 614 having a different spectrum. At time T7, the beam may be turned off.

Figure 8:
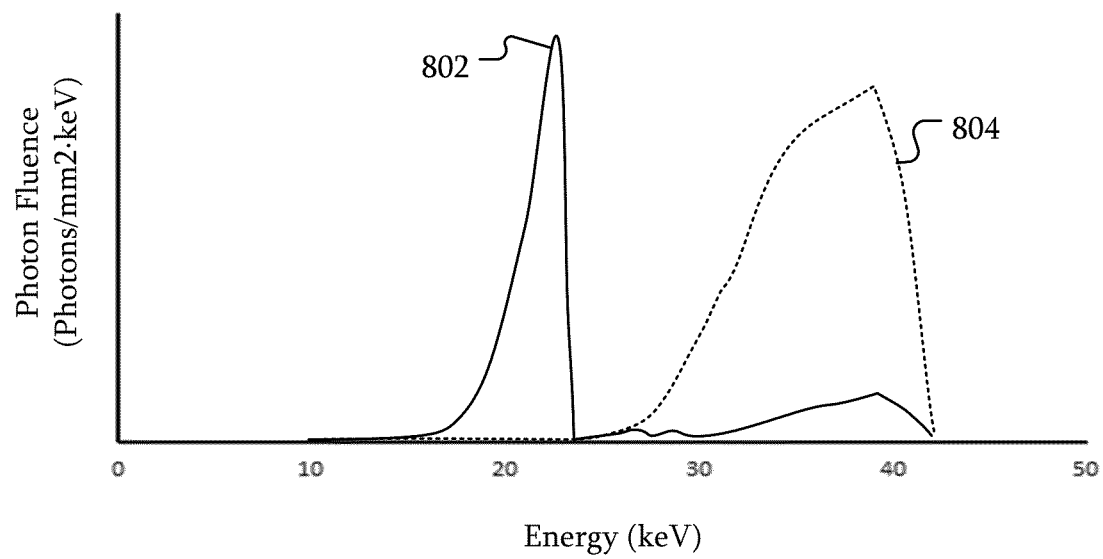
FIG. 8 is a chart of energy spectrums of an x-ray beam after different prefilter regions according to some embodiments.

FIG. 8 is a chart of energy spectrums of an x-ray beam after different prefilter regions according to some embodiments. Referring to FIGS. 6A, 6B, 7A, and 8, in this example, two spectrums 802 and 804 are illustrated, corresponding to filter regions 621 and 622. Accordingly, for the time from T1 to T3, the spectrum 802 is the spectrum of the filtered x-ray beam 614 due to filter region 621 while from time T3 to T7 the spectrum 804 is the spectrum of the filtered x-ray beam 614 due to filter region 622.

However, the exposure of the imager 640 may be integrated over the entire time from T1 to T7. While divided in time, the net spectrum received by the imager 640 may be the sum of the spectrums 802 and 804. In some embodiments, because the filter regions 621 and 622 may be specifically selected to generate a desired spectrum, multiple distinct local maximums may be created in the net spectrum by changing the time each pre-filter is in the x-ray beam.

Figure 9:
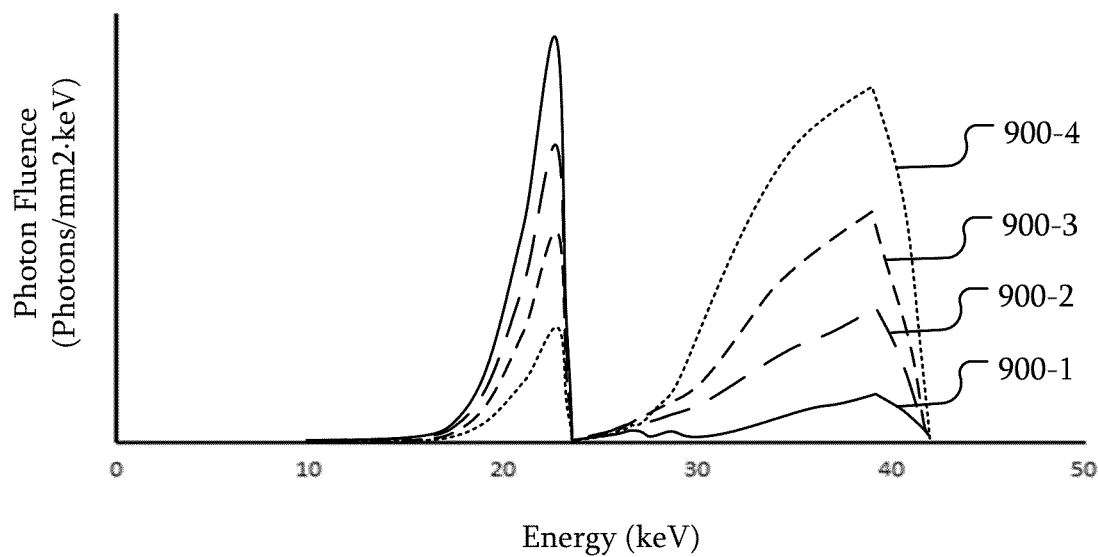
FIG. 9 is a chart of resulting energy spectrums of an x-ray beam after using pre-filter regions with different time ratios according to some embodiments.

FIG. 9 is a chart of resulting energy spectrums of an x-ray beam after using prefilter regions with different time ratios according to some embodiments. Referring to FIGS. 6A, 6B, 7A, and 9, the control logic 650 may be configured to control a difference in an amount of time that the x-ray beam passes through the filter regions. For example, the control logic 650 may control a ratio of an amount of time the x-ray beam 610 passes through the first region 621 vs the second region 622. The spectrums 900-1, 900-2, 900-3, and 900-4 represent different ratios of 0.1, 0.3, 0.5, and 0.7, respectively. While particular ratios and discrete steps in ration have been used as examples, the ratio may be different and also may be continuously variable based on the amount of time spent on each filter region.

A result of the different ratios is that the net spectrum may be controlled. Here, the balance between the lower energy components and the higher energy components may be controlled by adjusting the ratio. Some of the ratios, such as 0.7, may result in a spectrum that is not achievable by a single static filter.

The ratio may be changed for any variety of conditions. In some embodiments, the ratio may be changed from exposure to exposure. In other embodiments, the ratio may be changed based on the patient, the type of procedure, the sample, or the like. In other embodiments, the ratio may be a factory setting and/or a field calibration value that may or may not be accessible to normal users of the system 600.

Figure 7B:
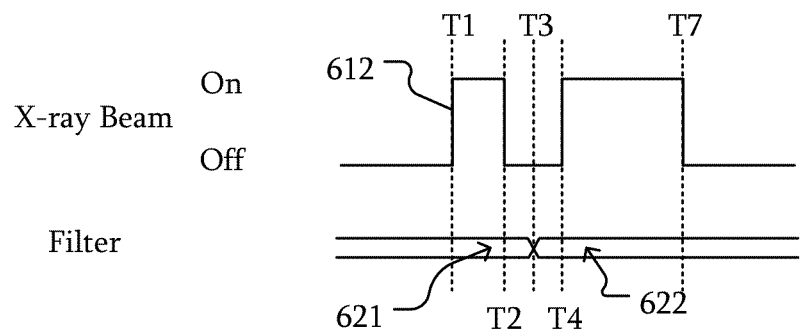

Referring back to FIG. 7A, the x-ray beam 612 is on during a time that the filter regions are moved to position region 622 in the x-ray beam 612. As a result, some artifacts may be generated. Referring to FIG. 7B, in some embodiments, the x-ray beam 612 may be pulsed such that the x-ray beam is off when the filter region is changed. For example, the x-ray beam 612 may be turned on at time T1. At time T2, the x-ray beam 612 is turned off. At time T3 the position of the regions of the filters is changed so that region 622 will be fully in the x-ray beam 612 when it is turned on. At time T4, the x-ray beam 612 is turned on and turned off at time T7. As a result, artifacts due to the transition of the filter regions maybe be reduced or eliminated. Although the x-ray beam 612 may be pulsed, the imager 640 may continue operating in a single exposure.

Figure 7C:
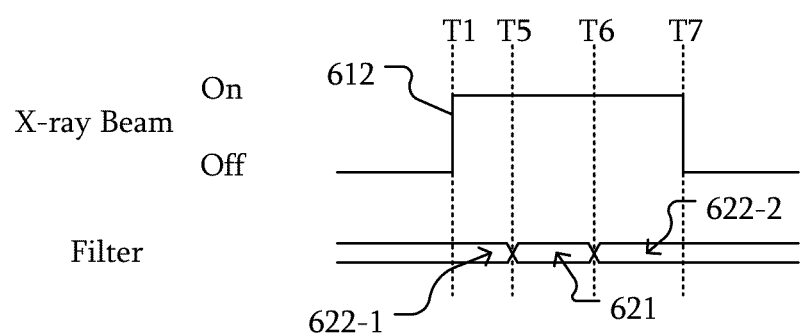

Referring to FIG. 7C, in some embodiments, a different structure and the position of the filter regions may be changed to reduce the artifacts of a transition in a different manner. Here, the x-ray prefilter 620 includes three regions where one is the region 621 and two regions 622-1 and 622-2 are similar to region 622, i.e. having the same characteristics of region 622. The x-ray beam 612 is turned on while region 622-1 is in the x-ray beam 612. At time T5, the x-ray prefilter 620 is moved to position region 621 in the x-ray beam 612. At time T6, the x-ray prefilter 620 is moved to position region 622-2 in the x-ray beam 612. At time T7 the beam is turned off. As a result, the transition from region 622-1 to 621 is complemented with a transition from region 621 to region 622-2.

Figure 7D:
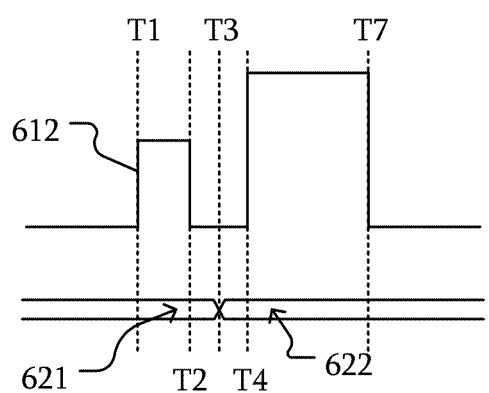

Referring to FIGS. 6A, 6B, and 7D, in some embodiments, the character of the x-ray beam 612 may be changed. For example, the operation in FIG. 7D may be similar to that of FIG. 7B; however, from time T1 to time T2, the x-ray source 610 may be operated to give the x-ray beam 612 having a first set of characteristics. From time T4 to T7, the x-ray source 610 may be operated to give the x-ray beam 612 a second set of characteristics that are different from the first set. For example, the x-ray source current and/or x-ray source 610 voltage, or the like may be changed to accommodate a difference between nominal transmissions through the regions 621 and 622. In another example, the x-ray source 610 may be operated to generate the x-ray beam 612 with a different spectrum that, when filtered by a different filter region, generates an output spectrum in the x-ray beam 614 with desired characteristic, such as a greater concentration in a particular energy range.

Figure 10A:
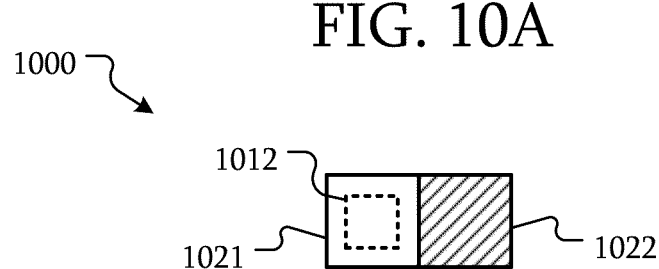
FIGS. 10A-13C are block diagrams of movable x-ray filters according to some embodiments.
Figure 10B:
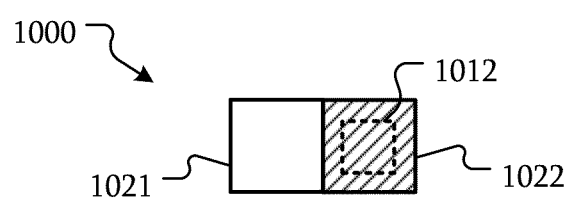

FIGS. 10A-13C are block diagrams of movable x-ray filters according to some embodiments. Each of these movable x-ray filters may be used as the x-ray prefilter 620 described above. Referring to FIGS. 10A and 10B, in some embodiments, the movable x-ray filter 1000 may include two regions 1021 and 1022, similar the movable x-ray filter 620 with regions 621 and 622 shown in FIGS. 6A-7B and 7D. At a beginning of an operation an x-ray beam 1012 may pass through region 1021 as illustrated in FIG. 10A. The filter 1000 may be translated so that region 1022 is positioned as illustrated in FIG. 10B such that the x-ray beam 1012 passes through the region 1022.

Figure 11A:
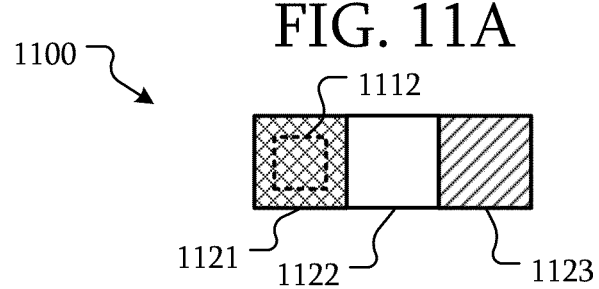
Figure 11B:
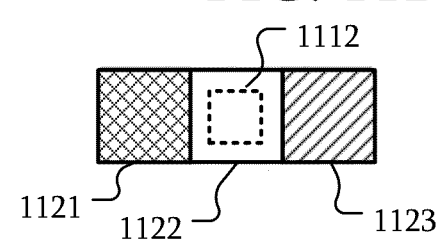
Figure 11C:
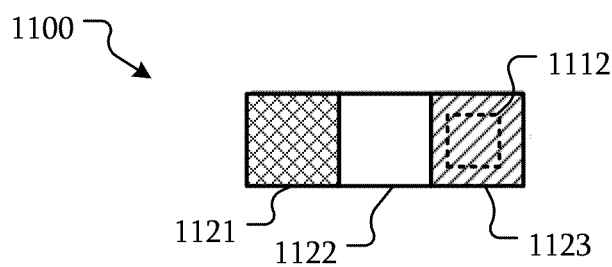

Referring to FIGS. 11A-11C, in some embodiments, the movable x-ray filter 1100 may include three regions 1121, 1122, and 1123, similar the movable x-ray filter 620 with regions 622-1, 621, and 622-2 shown in FIG. 7C. Here, regions 1121 and 1123 have the same filter characteristics; however, in other embodiments, the attenuation characteristics may be different. FIGS. 11A-C illustrate the translation of the filter 1100 through the x-ray beam 1112 such that the x-ray beam 1112 passes through region 1121 first, then region 1122, and finally region 1123.

Figure 12A:
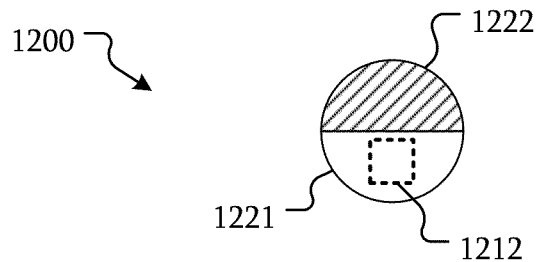
Figure 12B:
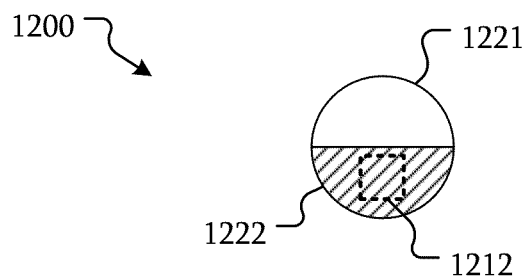
Figure 12C:
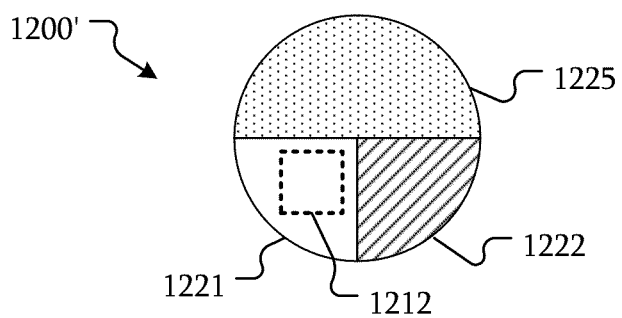

Referring to FIGS. 12A-12C, in some embodiments, the filter regions may be moved by rotation. Here, two regions 1221 and 1222 are illustrated, similar the movable x-ray filter 620 with regions 621 and 622 shown in FIGS. 6A-7B and 7D; however, any number of filter regions may be used. In FIG. 12A, the x-ray beam 1212 passes through region 1221. The x-ray filter 1200 is rotated so that region 1222 is in the path of the x-ray beam 1212 as illustrated in FIG. 12B. As illustrated in FIG. 12C, in some embodiments, the filter 1200' has two filter regions 1221 and 1221, but less than all of the filter 1200 includes filter regions. In this example, one half of the filter 1200 does not have a filter, has a material that blocks x-rays, has a material that passes x-rays, or the like.

Figure 13A:
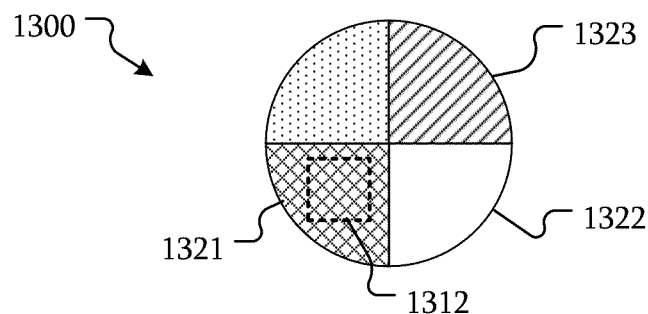
Figure 13B:
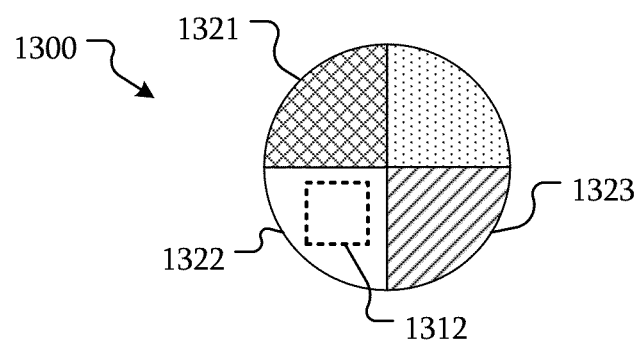
Figure 13C:
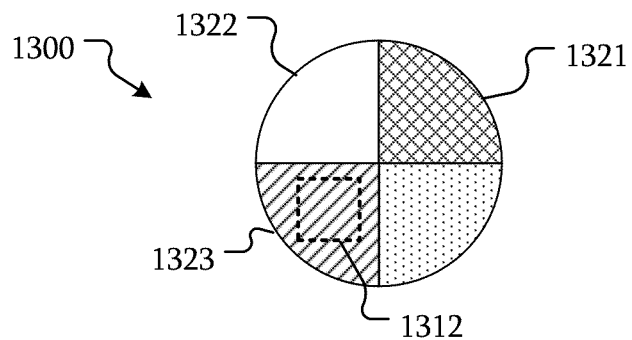

Referring to FIGS. 13A-13B, the filter 1300 may be configured similar to the filter 1100 with three regions 1321, 1322, and 1323, similar the movable x-ray filter 620 with regions 622-1, 621, and 622-2 shown in FIG. 7C. However, rather than translation, rotation is used to move one of the three regions into the path of the x-ray beam 1312. As illustrated by the change from FIGS. 13A to 13B to 13C, the filter 1300 may be rotated to bring one of the three regions 1321, 1322, and 1323 into the x-ray beam 1312. While three has been used as an example, in other embodiments, any number of filter regions may be present.

Referring to FIG. 6A, in some embodiments the x-ray prefilter 620 may be configured to rotate. In other embodiments, the x-ray filter may be configured to translate. In other embodiments, the x-ray prefilter 620 may be configured to rotate, translate, and/or move in an arbitrary manner as desired.

In some embodiments, the acquisition may occur over a time period from about 5 milliseconds (ms) to about 5 seconds. During this time period, the movable x-ray prefilter 620 may change position once or multiple times. In a particular example, the switching of the filter regions described above may be repeated during a single exposure. Using FIG. 7A as an example, at time T7, rather than the x-ray beam 612 being switched off, the x-ray prefilter 620 may be moved to place region 621 back in the x-ray beam 612. In a particular example, the linear filter 1000 may be moved in a reciprocating manner. In another example, the circular filter 1200 may be continuously rotated. Regardless, the movable x-ray prefilter 620 may change position multiple times over the exposure period.

In some embodiments, the movement of the x-ray prefilter 620 may change for one or more later operations of the x-ray source 610. For example, referring to FIGS. 6A, 10A, and 10B, the x-ray prefilter 620 may be moved such that in one operation of the x-ray source 610, the region 621 is placed in the x-ray beam 612 for a longer time than region 622. In the next operation of the x-ray source 610, the region 621 is placed in the x-ray beam 612 for a shorter time than region 622. As a result, the different operations of the combination of the x-ray source 610 and x-ray prefilter 620 may generate the x-ray beam 614 with different effective energy spectrums. In addition, in some embodiments, the resulting images generated by the different spectrums may be combined together.

While the operation of the x-ray source 610 has been described as being pulsed on and off, in other embodiments, the x-ray source 610 may be operated continuously.

Figure 14A:
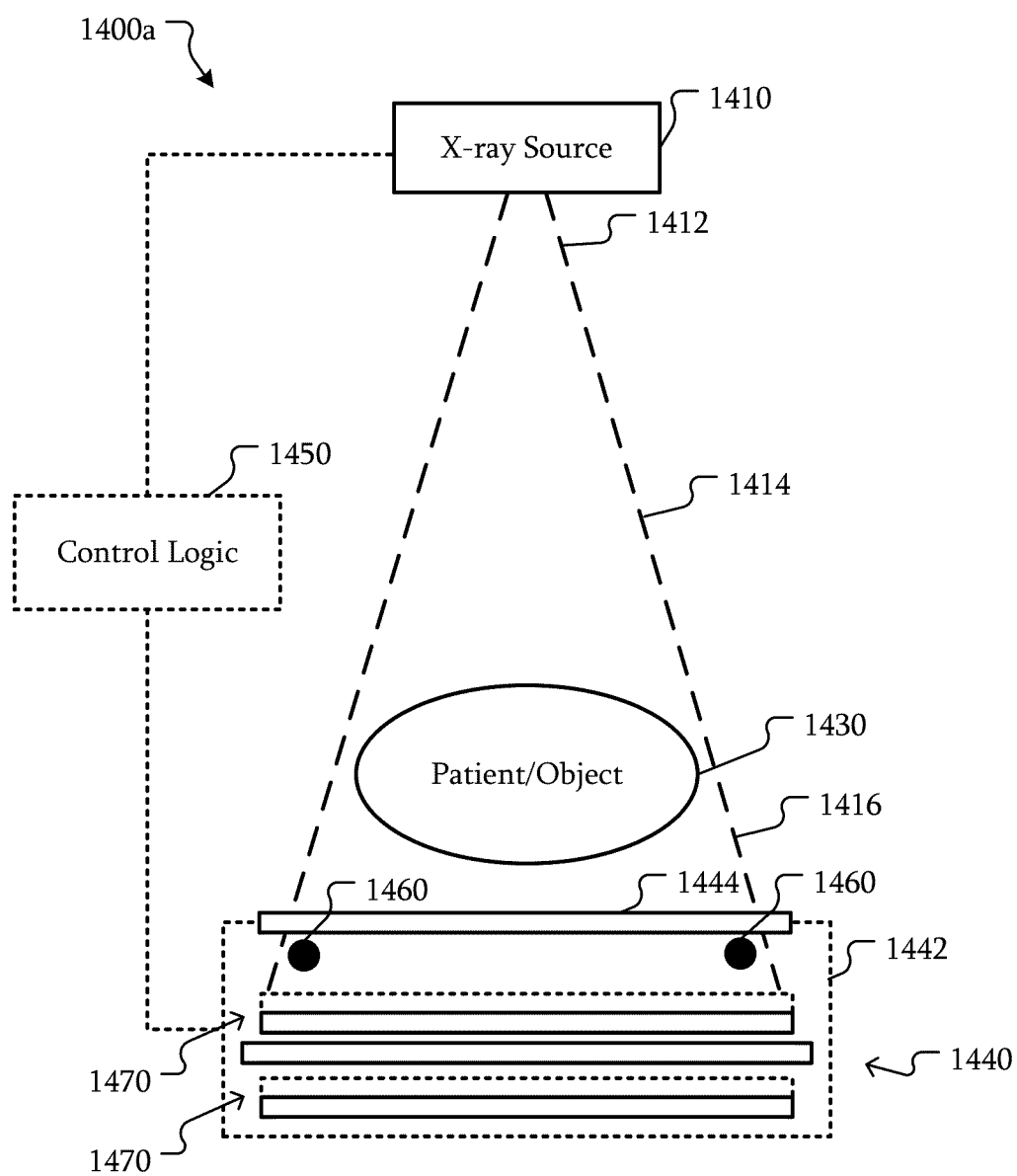
FIGS. 14A-14E are block diagrams of x-ray imaging systems including markers according to some embodiments.

FIGS. 14A-14E are block diagrams of x-ray imaging systems including markers according to some embodiments. Referring to FIG. 14A, in some embodiments, the x-ray imaging system 1400*a* may include an x-ray source 1410 configured to generate an x-ray beam 1412 and an imager 1440 similar to the corresponding portions of the x-ray imaging systems 100, 600, or the like described above. However, the x-ray imaging system 1400*a* may not include an x-ray prefilter such as the x-ray prefilters 120, 620, 1000, 1100, 1200, 1300, or the like described above.

The x-ray imaging system 1400*a* includes an x-ray imager 1440 similar to the x-ray imagers 140, 500, 640, or the like described above. The x-ray imager 1440 includes a housing 1440. Multiple imaging layers, such as imaging layers 1470 may be disposed in the housing 1440 overlapping each other. While two imaging layers 1470 are used as an example, in other embodiments, the number of imaging layers 1470 may be greater than two. The imaging layers 1470 may be similar to the imaging layers 510, 530, or the like as described above and may include associated sensor arrays, scintillators, or the like. Each imaging layer 1470 may be configured to generate an image in response to a corresponding incident x-ray beam 1416. The housing 1442 may include a window 1444 configured to allow x-rays to pass through the housing 1442 to the imaging layers.

Multiple x-ray markers 1460 may be disposed in the housing 1442. The x-ray markers 1460 may be disposed in a position to affect the incident x-ray beam 1416 for each of the imaging layers 1470. For example, the x-ray markers 1460 may be disposed such that the x-ray beam 1416 is incident on the x-ray markers 1460 before any of the imaging layers 1470. As a result, the x-ray markers 1460 may leave a shadow in an image generated by each of the imaging layers 1470. Although the x-ray markers 1460 are illustrated as being disposed before any of the imaging layers 1470, in other embodiments, some imaging layers 1470 may be disposed on the opposite side of the x-ray markers 1460.

In some embodiments, the control logic 1450 may be configured to combine the images from the imaging layers 1470. The control logic 1450 may be configured to spatially rotate, translate, scale, and/or perform arithmetic and/or non-linear operations on the images by processing the values of the pixels in whole or in parts. Such processing may include adding, subtracting, dividing, multiplying, non-linear operations, or the like. The particular operations selected, the parameters of the operations, or the like may be selected based on the locations of the shadows of the markers 1460 in the images.

Figure 14B:
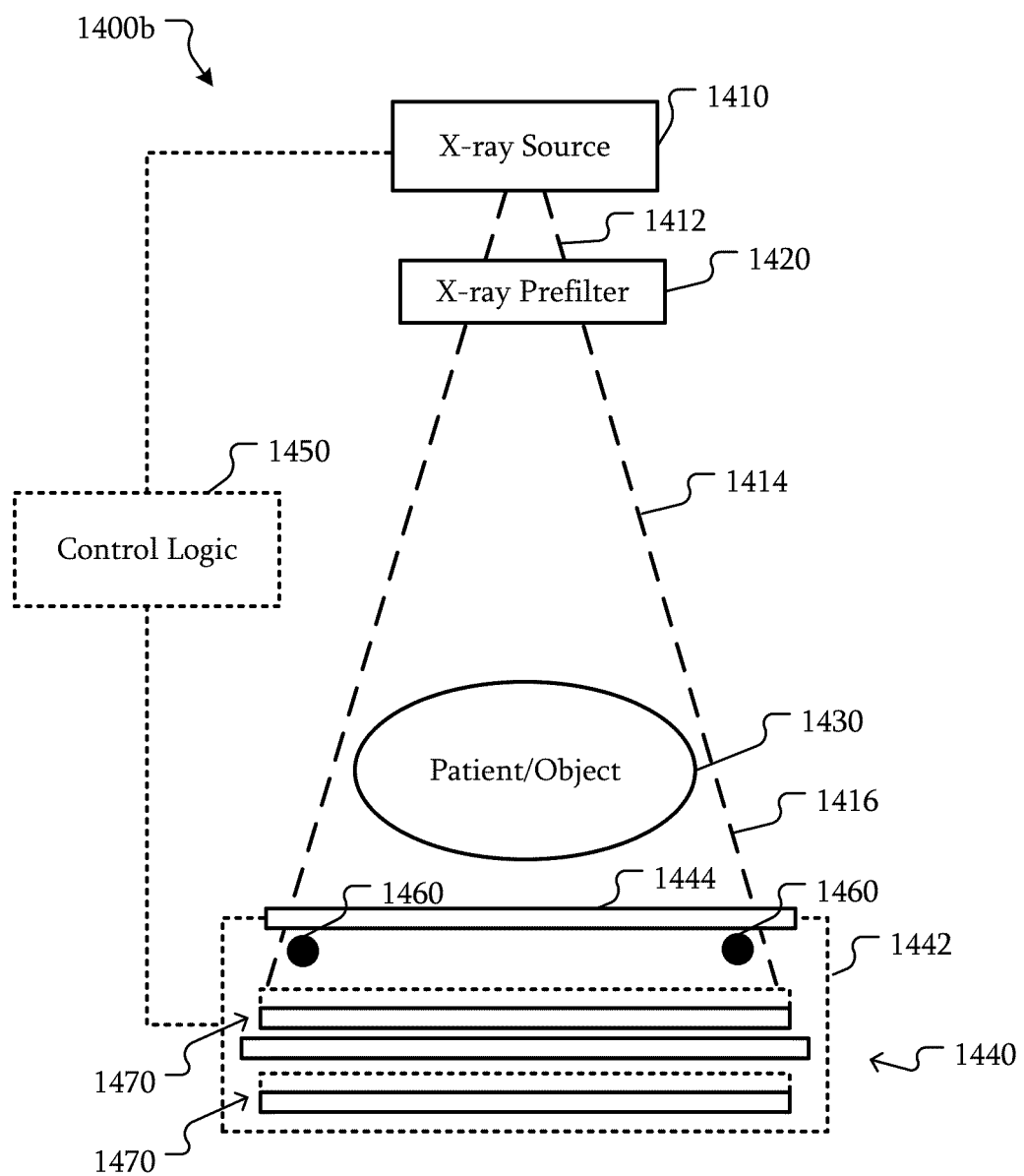

Referring to FIG. 14B, in some embodiments, the x-ray imaging system 1400*b* may be similar to the x-ray imaging system 1400*a* of FIG. 14A. However, the x-ray imaging system 1400*b* may include an x-ray prefilter 1420 similar to the x-ray prefilter 120 or the like as described above, or a different type of prefilter.

Figure 14C:
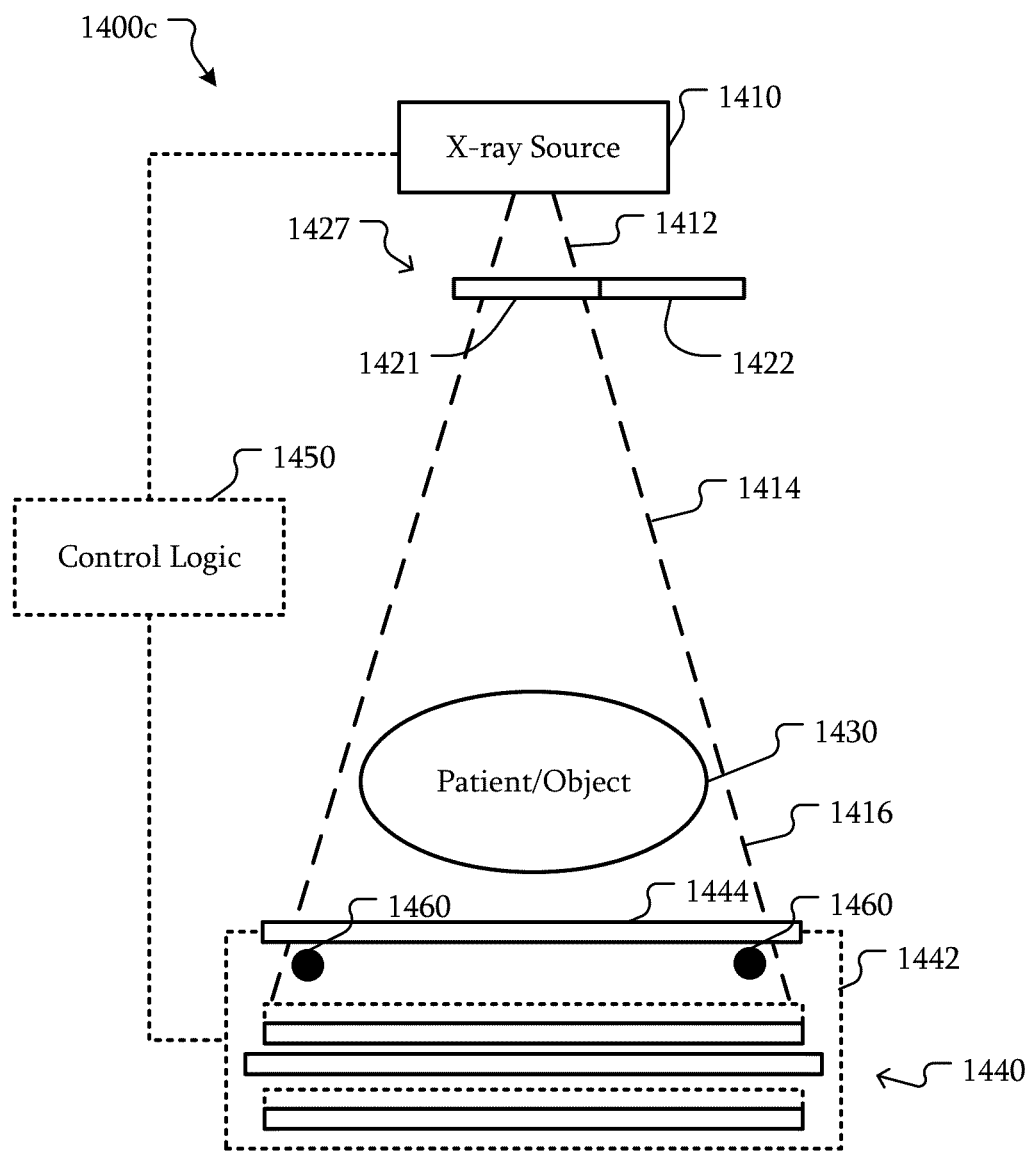

Referring to FIG. 14C, in some embodiments, the x-ray imaging system 1400*c* may be similar to the x-ray imaging system 1400*a* of FIG. 14A. However, the x-ray imaging system 1400*c* may include a movable x-ray prefilter 1427 similar to the movable x-ray prefilter 120, 620, 1000, 1100, 1200, 1300, or the like described above.

With multi-layer imagers 1440, an image generated by each imaging layer 1470 may be different from another layer by a scaling factor, a position, and/or a rotation. The scaling factor may result from the position of a particular imaging layer 1470 and the expanding nature of the x-ray beam 1416. Manufacturing tolerances, thermal cycling, or the like may contribute to position and/or orientation changes that also affect registration of images generated by the imaging layers 1470.

An offline calibration procedure may be performed with a removable calibration pattern used in place of a patient or object 1430. However, a calibration performed in this manner may only be valid for a particular orientation of the x-ray beam 1416 and the imager 1440. In particular, if the x-ray focal spot position changes, the calibration may no longer be valid. Calibration patterns such as x-ray markers and/or phantoms are only temporary. These calibration procedures may only be performed periodically because of the time and effort involved in the procedure. During this procedure, the system may not be used for imaging patients or objects 1430.

However, as the x-ray markers 1460 are within the housing 1442 and integrated with the imager 1440, the x-ray markers 1460 may be present in images generated during normal operations. The affects of the x-ray markers 1460 in the images may be used to align those images. Having shadows from x-ray markers 1460 in an image of the patient or object 1430 may be undesirable as the shadows may obscure features of the patient or object 1430 in those regions leading to potential misdiagnosis. However, in some embodiments, such as when the imaging system 1400*a*, 1400*b*, or 1400*c* is used for mammography, portions of an image may not be affected by the patient 1430.

In some embodiments, only two x-ray markers 1460 are disposed in the housing 1442. Two x-ray markers 1460 may provide enough information in the images from the imaging layers 1470 to rotate, translate, and scale the images, assuming that the imaging layers 1470 are substantially parallel. In other embodiments, a different number of x-ray markers 1470 may be used to improve accuracy.

In some embodiments, the x-ray markers 1460 may be substantially opaque to x-rays. For example, the x-ray markers 1460 may absorb about 90% or more of incident x-rays. In other embodiments, the x-ray markers 1460 may be partially transparent to x-rays. For example, the x-ray markers 1460 may have an absorption percentage from about 10% to about 90%. As a result, while the x-ray markers 1460 may leave a shadow in the images, at least some x-rays may reach the imaging layers 1470. This affect may be calibrated out by adjusting the gain for pixels of the imaging layers 1470 that are in the shadow of the x-ray markers 1460.

In some embodiments, at least one of the x-ray markers 1460 includes one or more materials having a k-edge in the x-ray spectrum. Such material may allow the contrast level to be similar in different imaging layers. For example, when the x-ray beam 1414 has a dual-maximum energy spectrum, a material may be selected to have a k-edge between the two maximums. As a result, the aggregate attenuation of each local maximum in the spectrum may be similar, such as 40%/50% or 20%/30% attenuation for two different energy ranges. In some embodiments, the material and/or materials may be specifically selected such that the contrast introduced by the x-ray markers 1460 is substantially the same in two or more of the imaging layers.

Figure 14D:
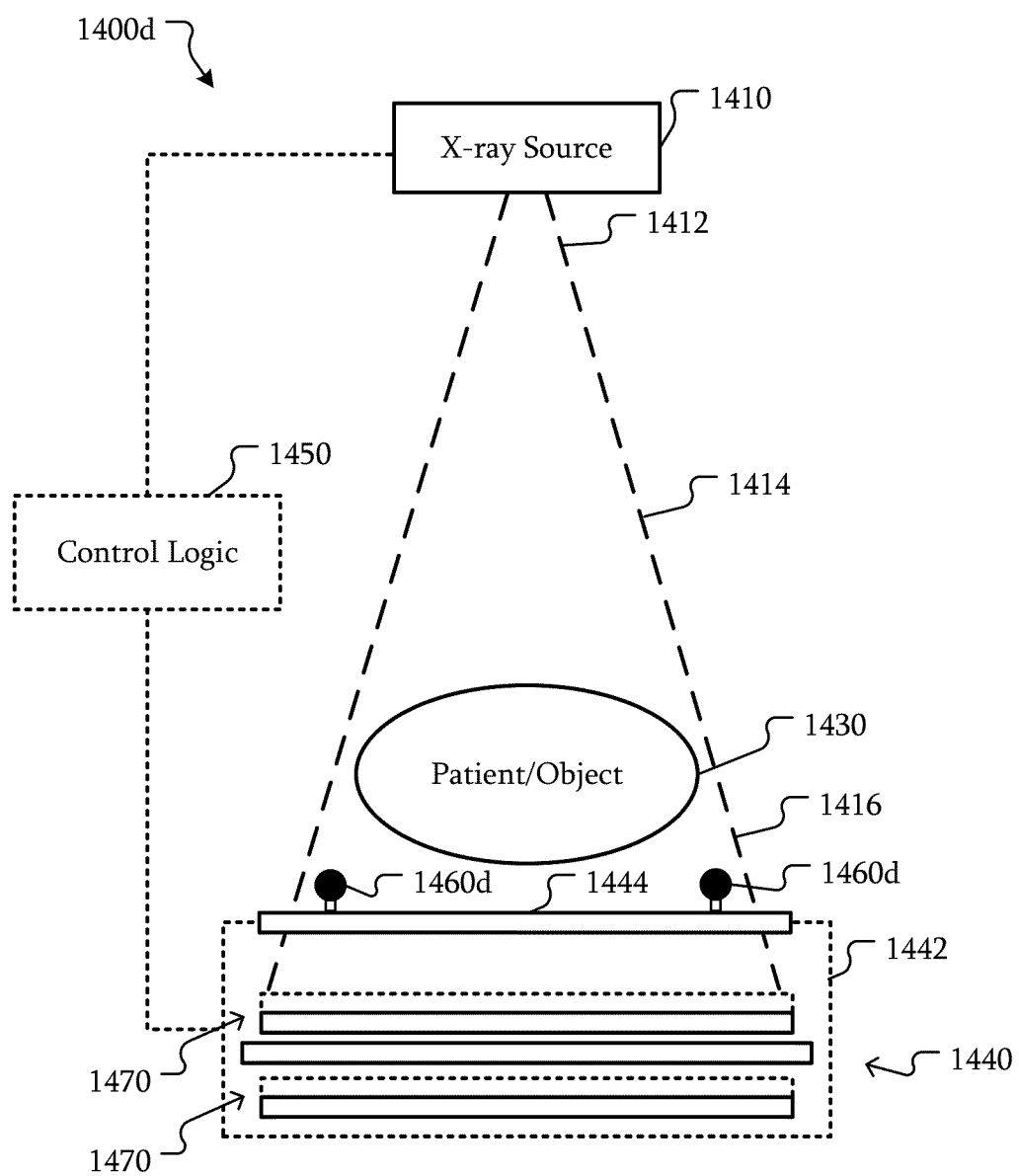

Referring to FIG. 14D, the imaging system 1400*d* may be similar to the imaging systems 1400*a*, 1400*b*, 1400*c*, or the like as described above. However, in some embodiments, the x-ray markers 1460*d* are disposed outside of the housing 1442. In some embodiments, the x-ray markers 1460*d* are attached to the housing 1442 such that the x-ray markers 1460d are disposed within the x-ray beam 1414. The x-ray markers 1460d may be otherwise similar to those described herein.

Figure 14E:
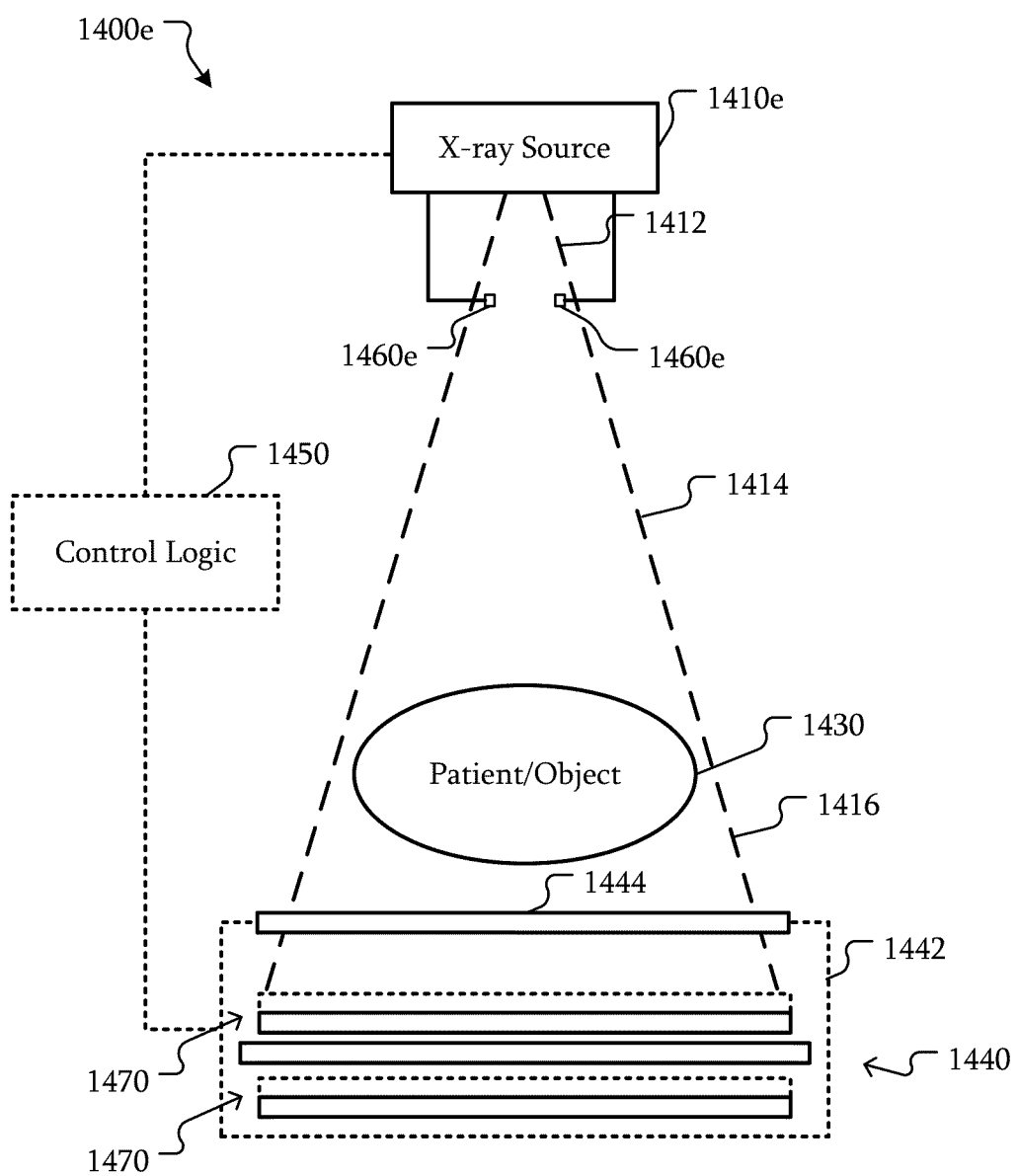

Referring to FIG. 14E, the imaging system 1400e may be similar to the imaging systems 1400a, 1400b, 1400c, 1400d, or the like as described above. However, in some embodiments, the x-ray markers 1460e are attached to the x-ray source 1410e or a collimator (not shown) attached to the x-ray source 1410e. The x-ray markers 1460e are attached to the x-ray source such that the x-ray markers 1460e are disposed in the x-ray beam 1414. While the x-ray markers 1460e are illustrated as being disposed on the exterior of the x-ray source 1410e, in other embodiments, the x-ray markers 1460e may be disposed within the x-ray source 1410e.

Figure 15:
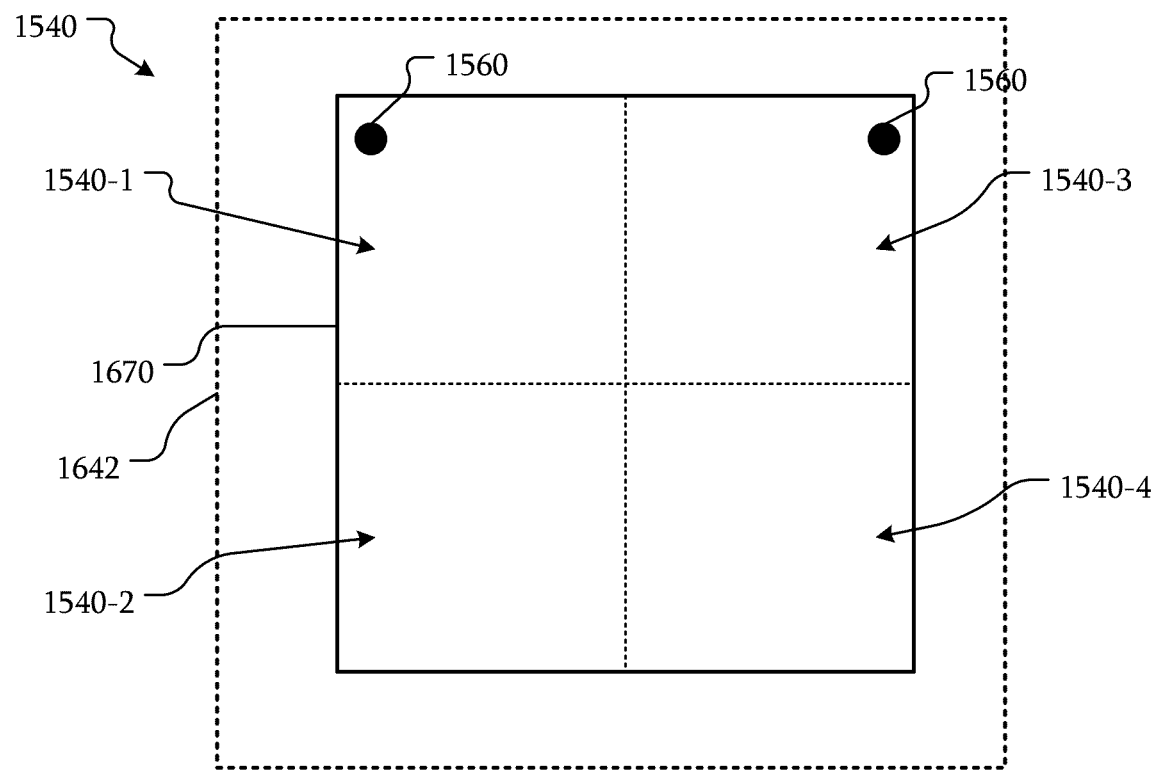
FIG. 15 is a plan view of an imaging system including markers according to some embodiments.

FIG. 15 is a plan view of an imaging system including markers according to some embodiments. In some embodiments, the imager 1540 may be similar to the imager 1440 of FIGS. 14A-14C. Here, a rectangle formed by four quadrants 1560-1 to 1560-4 represents the imagable region of the imager 1540 formed by a rectangular sensor array of the imaging layers (not illustrated). The x-ray markers 1560 are disposed relative to the imaging layers such that shadows of the x-ray markers 1560 appear in at least two quadrants of the resulting images. Here, the x-ray markers 1560 are disposed to overlap with quadrants 1540-1 and 1540-3. While these quadrants are used as examples, the x-ray markers 1560 may be disposed in different arrangements and/or different quadrants.

In some embodiments, the positions of the x-ray markers 1560 are fixed relative to the imaging layers. While the x-ray markers 1560 may move slightly over time due to mechanical tolerances, thermal stress, or the like, the x-ray markers 1560 may still be fixed relative to the imaging layers during an imaging operation.

While the x-ray markers 1560 have been described as being disposed in different quadrants, in some embodiments, multiple x-ray markers 1560 may be disposed in a single quadrant, in a single corner, or the like.

Figure 16:
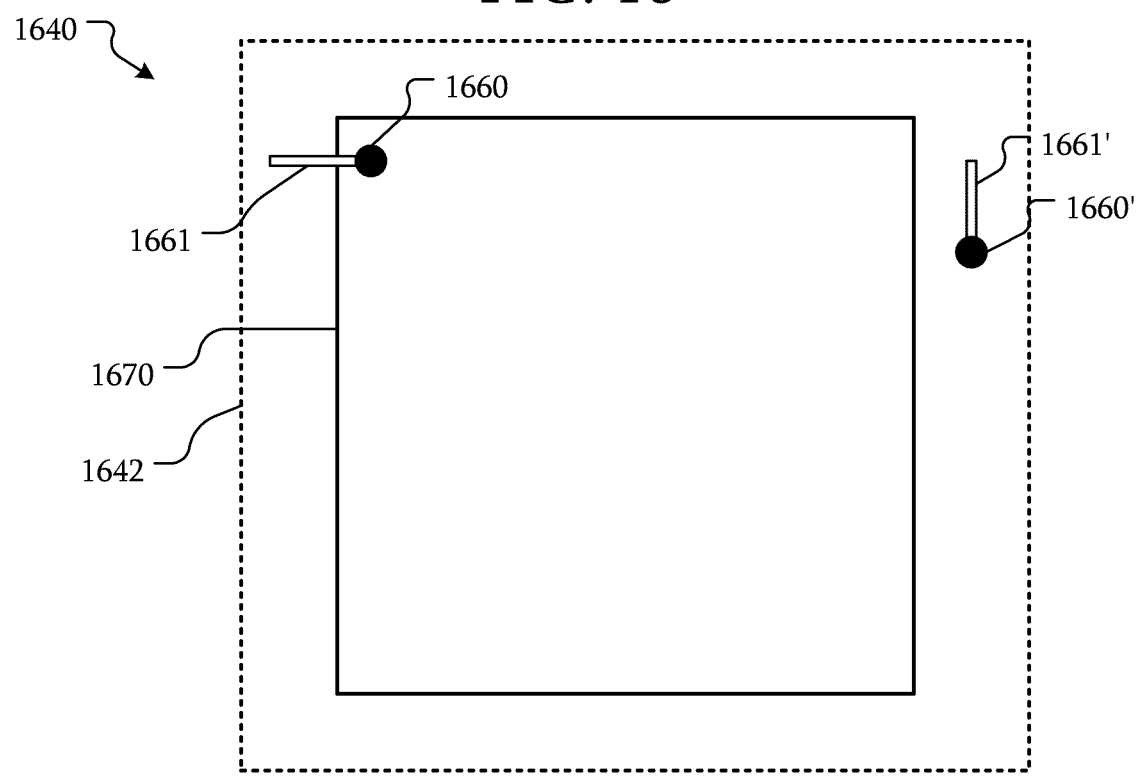
FIG. 16 is a plan view of an imaging system including movable markers according to some embodiments.

FIG. 16 is a plan view of an imaging system including movable markers according to some embodiments. Ins some embodiments, the imager 1640 may be similar to the imager 1440, 1540, or the like described above. However, the positions of the x-ray markers 1660 may be movable relative to the imaging layers (not illustrated). For example, each x-ray marker 1660 and 1660' is mounted to an associated movable structure 1661 and 1661', respectively. The movable structures 1661 and 1661' may include solenoids, motors, slides, hinges, gears, or the like to change the position of the associated x-ray markers 1660 and 1660'. Here, x-ray marker 1660 is illustrated as being in a position in the imagable field of the imager 1640. However, x-ray marker 1660' has been moved to be outside of the imagable field of the imager 1640. That is, the x-ray markers 1660 may be movable within the housing 1642 to not overlap the imaging layers of the imager 1640. Thus, the x-ray marker 1600' may not cast an x-ray shadow on imaging layers of the imager 1640. In some embodiments, the x-ray markers 1660 and 1660' may both be moved outside of the imagable filed of the imager 1640 during a calibration procedure and inside during normal operation. The x-ray markers 1660 and 1660' may be movable independently, in conjunction, or the like. In addition, in some embodiments, the x-ray markers 1660 and 1660' may be movable only within the imagable field of the imager 1640.

In some embodiments, the movable structures 1661 and 1661' may be formed from a material that is substantially transparent to x-rays. For example, the movable structures 1661 and 1661' may include plastic, glass, carbon, composites, combinations of such materials, or the like. The movable structures 1661 and 1661' may include a substrate formed of such materials on which the x-ray markers 1600 are mounted.

In some embodiments, the x-ray markers 1660 and the movable structures 1661 and 1661' may be disposed outside of and attached to the housing 1642 similar to the x-ray markers 1460d described above. The x-ray markers 1660 may still be movable to be placed in or out of the x-ray beam.

In some embodiments, the x-ray markers may have a variety of shapes. FIGS. 17A-18B show a variety of examples of x-ray markers. However, x-ray markers are not limited to these particular shapes.

While various features of x-ray markers have been described with respect to the imagers 1440, 1540, 1640, or the like, x-ray markers mounted to an x-ray source such as x-ray makers 1460e may include similar features. Moreover, in some embodiments, x-ray markers may be disposed on both an x-ray source and an imager such as on x-ray source 1410 and imager 1440.

Figure 17A:
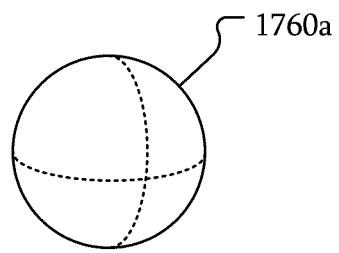
FIGS. 17A-17C are diagrams of markers according to some embodiments.
Figure 17B:
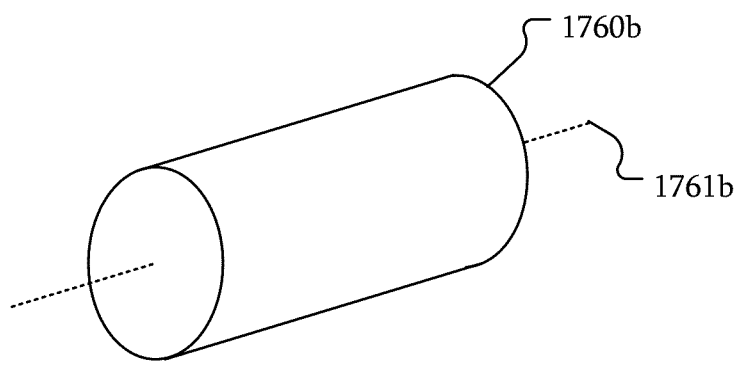
Figure 17C:

FIGS. 17A-17C are diagrams of markers according to some embodiments. Referring to FIG. 17A, in some embodiments, one or more x-ray markers 1760a may have a spherical shape. A spherical shape may have a shadow that is a circle that is substantially independent of the angle of incidence. While the resulting image may vary from a circle to an oval based on the relative angle of the incident x-ray beam to the imaging layer, the x-ray marker 1760 itself will have a reduced or eliminated impact on the shape.

Referring to FIG. 17B, in some embodiments, the x-ray marker 1760b may have a cylindrical shape. The cylindrical shape of the x-ray marker 1760b may have a major axis 1761b. As will be described in further detail below, the major axis 1761b may be substantially parallel to a major axis of an imaging layer, such as an X or Y axis of the imaging layer.

Referring to FIG. 17C, in some embodiments, the x-ray marker 1760c may have a disk shape.

Figure 18A:
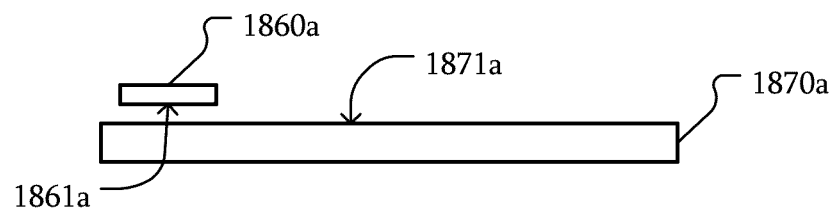
FIG. 18A-18B is a plan view of an imaging system including examples of orientations of markers according to some embodiments.
Figure 18B:
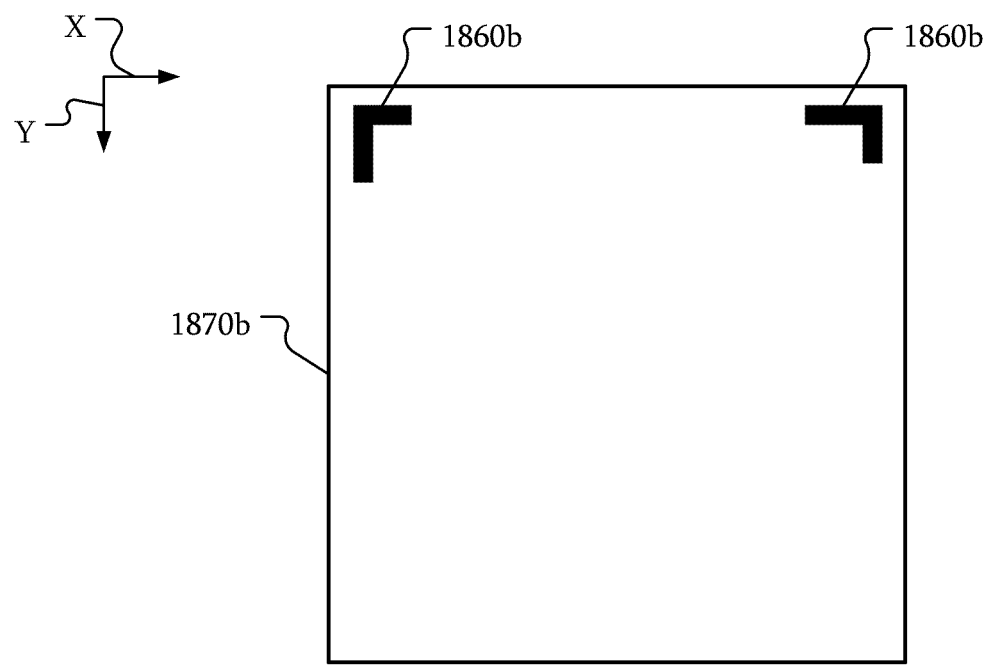

FIG. 18A-18B is a plan view of an imaging system including examples of orientations of markers according to some embodiments. The imaging layers 1870 may be part of the imagers 1440 or the like described above. Referring to FIG. 18A, the imaging layer 1870a includes an imaging surface 1871a. The imaging surface 1871a is the surface containing an array of imaging sensors or is parallel to such an array.

In some embodiments, the x-ray marker 1860a has a rectangular prism shape. The x-ray marker 1860a has a side 1861a that is parallel to the imaging surface 1871a. In a particular example, the x-ray marker 1860a may have a shape of a sheet that is disposed parallel to the imaging surface 1871a.

Referring to FIG. 18B, in some embodiments, the x-ray markers 1860b may be at least somewhat non-symmetrical and/or irregular. As illustrated, the x-ray markers 1860b have an L-shape with one leg extending in one direction and another leg extending in a perpendicular direction. The legs of x-ray markers 1860b are aligned to the X and Y axes of the imaging surface of the imaging layer 1870b. Here, different legs of the x-ray markers 1860b are aligned to individual axes; however, in other embodiments, the same legs of the x-ray markers 1860b may be aligned to the same axis. For example, a shorter leg of the L-shaped x-ray markers 1860b may be aligned with the X-axis.

As described above, the x-ray markers may have a variety of different shapes. In some embodiments, at least one of the x-ray markers has a shape or orientation different from another marker of the markers. For example, the x-ray markers may be the same, but rotated differently, such as in FIG. 18B. In some embodiments, the x-ray markers may each be different.

In some embodiments, multiple x-ray markers, whether different or the same, may be disposed in substantially one location, such as a single corner and/or a single quadrant. In addition, one or more other markers may be disposed in other locations. While a variety of shapes have been used as examples, in other embodiments, the shapes may take forms different from those above. The shapes may have zero to multiple axes of symmetry. Shapes with one or more axes of symmetry are not limited to those shapes described above.

Some embodiments include an x-ray system, comprising: an x-ray imager 140, 640, 1440, 1540, 1640 including a plurality of imaging layers 510, 530; an x-ray source 110, 610, 1410 configured to generate an x-ray beam; and an x-ray prefilter 120, 620, 1000, 1100, 1200, 1200', 1300, 1420, 1427; wherein: the x-ray prefilter 120, 620, 1000, 1100, 1200, 1200', 1300, 1420, 1427 is configured to adjust an energy spectrum of the x-ray beam to create or decrease a level of x-ray fluence of a local minimum between two of a plurality of local maximums.

In some embodiments, each of the imaging layers 510, 530 includes an x-ray conversion material 512, 532 associated with a corresponding one of the local maximums.

In some embodiments, the x-ray prefilter 120, 620, 1000, 1100, 1200, 1200', 1300, 1420, 1427 includes at least one material having a k-edge absorption between the two local maximums.

In some embodiments, the x-ray prefilter 120, 620, 1000, 1100, 1200, 1200', 1300, 1420, 1427 includes multiple materials, each having a different k-edge absorption.

In some embodiments, the x-ray prefilter 120, 620, 1000, 1100, 1200, 1200', 1300, 1420, 1427 includes a plurality of layers, each layer including one of the materials of the x-ray prefilter 120, 620, 1000, 1100, 1200, 1200', 1300, 1420, 1427.

In some embodiments, the x-ray prefilter 120, 620, 1000, 1100, 1200, 1200', 1300, 1420, 1427 includes at least one of a pure material, an alloy, and a powdered material.

In some embodiments, a first imaging layer of the imaging layers 510, 530 is disposed to receive the x-ray beam before a second imaging layer of the imaging layers 510, 530; each of the imaging layers 510, 530 includes an x-ray conversion material 512, 532 associated with a corresponding one of the local maximums; the x-ray conversion material 512 of the first imaging layer 510 is configured to absorb more of a first local maximum of the two local maximums than the x-ray conversion material 532 of the second imaging layer 530; and the x-ray conversion material 532 of the second imaging layer 530 is configured to absorb more of a second local maximum of the two local maximums than the x-ray conversion material 512 of the first imaging layer 510.

In some embodiments, an energy of the first local maximum is less than an energy of the second local maximum.

In some embodiments, each of the imaging layers 510, 530 includes an x-ray conversion material 512, 532 associated with a corresponding one of the local maximums; and thicknesses of the x-ray conversion materials of at least two of the imaging layers 510, 530 are different.

In some embodiments, an anode of the x-ray source 110, 610, 1410 includes at least two materials producing different x-ray spectrums.

In some embodiments, the x-ray system further comprises an x-ray filter 520 disposed between at least two of the imaging layers 510, 530.

Some embodiments include an x-ray system comprising: an x-ray source 110, 610, 1410 configured to generate an x-ray beam; a movable x-ray filter 620, 1000, 1100, 1200, 1200', 1300, 1427 including a plurality of filter regions, wherein at least one of the filter regions has an attenuation characteristic that is different from at least one of the other filter regions; and control logic 650, 1450 configured to move the x-ray filter 620, 1000, 1100, 1200, 1200', 1300, 1427 during an exposure.

In some embodiments, a first filter region of the filter regions is configured such that the x-ray beam has a first energy peak when filtered by the first filter region; a second filter region of the filter regions is configured such that the x-ray beam has a second energy peak when filtered by the second filter region; and an energy of the first energy peak is different from an energy of the second energy peak.

In some embodiments, the movable x-ray filter 620, 1000, 1100, 1200, 1200', 1300, 1427 is configured to at least rotate or translate.

In some embodiments, the control logic 650, 1450 is further configured to control a position of the movable filter 620, 1000, 1100, 1200, 1200', 1300, 1427 such that the x-ray beam passes through more than one of the filter regions during a single exposure.

In some embodiments, the control logic 650, 1450 is configured to adjust the x-rays source parameters during the single exposure corresponding to the position of the movable filter 620, 1000, 1100, 1200, 1200', 1300, 1427.

In some embodiments, the filter regions include a first filter region, a second filter region, and a third filter region; the first filter region is adjacent to the second filter region; the second filter region is adjacent to the third filter region; transmission characteristics of the first filter region and the third filter region are the same; and transmission characteristics of the second filter region are different from the transmission characteristics of the first and third filter regions.

In some embodiments, the x-ray system further comprises control logic 650, 1450 configured to control a difference in an amount of time that the x-ray beam passes through a first filter region of the filter regions and an amount of time the x-ray beam passes through a second filter region of the filter regions.

In some embodiments, the x-ray system further comprises an x-ray imager 140, 640, 1440, 1540, 1640 with one or more imaging layers 510, 530.

Some embodiments include an x-ray system, comprising: means for generating an x-ray beam; means for filtering the x-ray beam to have a multi-maximum energy spectrum; and means for converting at least a first part of the filtered x-ray beam into a first image; means for converting at least a second part of the filtered x-ray beam into a second image; and means for generating a third image based on the first image and the second image.

Examples of the means for generating an x-ray beam include the x-ray source 110, 610, 1410, or the like described above. Examples of the means for filtering the x-ray beam to have a multi-maximum energy spectrum include the x-ray prefilter 120, 620, 1000, 1100, 1200, 1200', 1300, 1427, or the like described above. Examples of the means for converting at least a first part of the filtered x-ray beam into a first image include the imaging layers 510 and 530, or the like described above. Examples of the means for converting at least a second part of the filtered x-ray beam into a second image the imaging layers 510 and 530, or the like described above. Examples of the means for generating a third image based on the first image and the second image include the control logic 650, 1450, or the like described above.

In some embodiments, the means for filtering the x-ray beam includes means for dynamically filtering the x-ray beam.

An x-ray imaging system, comprising: a housing; a plurality of overlapping imaging layers 510, 530 disposed in the housing, each imaging layer configured to generate an image in response to a corresponding incident x-ray beam; and a plurality of x-ray markers 1460, 1460*d*, 1560, 1660, 1760*a*, 1760*b*, 1760*c*, 1860*a*, 1860*b* 1460, 1460*d*, 1560, 1660, 1760*a*, 1760*b*, 1760*c*, 1860*a*, 1860*b* attached to the housing and disposed to affect the incident x-ray beam for each of the imaging layers 510, 530.

In some embodiments, each of the imaging layers 510, 530 includes a rectangular sensor array including four quadrants; the markers 1460, 1460*d*, 1560, 1660, 1760*a*, 1760*b*, 1760*c*, 1860*a*, 1860*b* are disposed relative to the imaging layers 510, 530 such that shadows of the markers 1460, 1460*d*, 1560, 1660, 1760*a*, 1760*b*, 1760*c*, 1860*a*, 1860*b* appear in at least two quadrants of the resulting images.

In some embodiments, positions of the markers 1460, 1460*d*, 1560, 1660, 1760*a*, 1760*b*, 1760*c*, 1860*a*, 1860*b* are fixed relative to the imaging layers 510, 530.

In some embodiments, positions of the markers 1460, 1460*d*, 1560, 1660, 1760*a*, 1760*b*, 1760*c*, 1860*a*, 1860*b* are movable relative to the imaging layers 510, 530.

In some embodiments, positions of the markers 1460, 1460*d*, 1560, 1660, 1760*a*, 1760*b*, 1760*c*, 1860*a*, 1860*b* are movable relative to the imaging layers 510, 530 such that the markers 1460, 1460*d*, 1560, 1660, 1760*a*, 1760*b*, 1760*c*, 1860*a*, 1860*b* may be moved to not cast an x-ray shadow on one or more of the imaging layers 510, 530.

In some embodiments, at least one of the markers 1460, 1460*d*, 1560, 1660, 1760*a*, 1860*a*, 1860*b* has a spherical shape.

In some embodiments, at least one of the markers 1460, 1460*d*, 1560, 1660, 1760*b*, 1860*a*, 1860*b* has a cylindrical shape.

In some embodiments, a major axis of the at least one of the markers 1460, 1460*d*, 1560, 1660, 1760*a*, 1760*b*, 1760*c*, 1860*a*, 1860*b* is parallel to a major axis of the imaging layers 510, 530.

In some embodiments, at least one of the markers 1460, 1460*d*, 1560, 1660, 1760*a*, 1760*b*, 1760*c*, 1860*a*, 1860*b* has a shape or orientation different from another marker of the markers 1460, 1460*d*, 1560, 1660, 1760*a*, 1760*b*, 1760*c*, 1860*a*, 1860*b*.

In some embodiments, at least one of the markers 1460, 1460*d*, 1560, 1660, 1760*c*, 1860*a*, 1860*b* has a disk shape.

In some embodiments, at least one of the markers 1460, 1460*d*, 1560, 1660, 1760*a*, 1760*b*, 1760*c*, 1860*a*, 1860*b* has a rectangular prism shape with a side parallel to an imaging surface of the imaging layers 510, 530.

In some embodiments, at least one of the markers 1460, 1460*d*, 1560, 1660, 1860*a*, 1860*b* includes a sheet disposed parallel to an imaging surface of the imaging layers 510, 530.

In some embodiments, at least one of the markers 1460, 1460*d*, 1560, 1660, 1760*a*, 1760*b*, 1760*c*, 1860*a*, 1860*b* includes an L shape with legs of the L shape being aligned to X and Y axes of an imaging surface of the imaging layers 510, 530.

In some embodiments, at least one of the markers 1460, 1460*d*, 1560, 1660, 1760*a*, 1760*b*, 1760*c*, 1860*a*, 1860*b* includes a material having a k-edge in the x-ray spectrum of the x-ray beam.

In some embodiments, at least one of the markers 1460, 1460*d*, 1560, 1660, 1760*a*, 1760*b*, 1760*c*, 1860*a*, 1860*b* is disposed within the housing.

In some embodiments, at least one of the markers 1460, 1460*d*, 1560, 1660, 1760*a*, 1760*b*, 1760*c*, 1860*a*, 1860*b* is disposed outside of the housing.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶6. Embodiments of the invention in which an exclusive property or privilege is claimed are defined as follows.

The invention claimed is:

1. An x-ray imaging system, comprising:
   a housing;
   a plurality of overlapping imaging layers disposed in the housing, each imaging layer configured to generate an image in response to a corresponding incident x-ray beam; and
   a plurality of x-ray markers attached to the housing and disposed to affect the incident x-ray beam for each of the imaging layers.

2. The x-ray system of claim 1, wherein
   each of the imaging layers includes a rectangular sensor array including four quadrants;
   the markers are disposed relative to the imaging layers such that shadows of the markers appear in at least two quadrants of the resulting images.

3. The x-ray system of claim 1, wherein positions of the markers are fixed relative to the imaging layers.

4. The x-ray system of claim 1, wherein positions of the markers are movable relative to the imaging layers.

5. The x-ray system of claim 1, wherein positions of the markers are movable relative to the imaging layers such that the markers may be moved to not cast an x-ray shadow on one or more of the imaging layers.

6. The x-ray system of claim 1, wherein at least one of the markers has a spherical shape.

7. The x-ray system of claim 1, wherein at least one of the markers has a cylindrical shape.

8. The x-ray system of claim 7, wherein a major axis of the at least one of the markers is parallel to a major axis of the imaging layers.

9. The x-ray system of claim 1, wherein at least one of the markers has a shape or orientation different from another marker of the markers.

10. The x-ray system of claim 1, wherein at least one of the markers has a disk shape.

11. The x-ray system of claim 1, wherein at least one of the markers has a rectangular prism shape with a side parallel to an imaging surface of the imaging layers.

12. The x-ray system of claim 1, wherein at least one of the markers includes a sheet disposed parallel to an imaging surface of the imaging layers.

13. The x-ray system of claim 1, wherein at least one of the markers includes an L shape with legs of the L shape being aligned to X and Y axes of an imaging surface of the imaging layers.

14. The x-ray system of claim 1, wherein at least one of the markers includes a material having a k-edge in the x-ray spectrum of the x-ray beam.

15. The x-ray system of claim 1, wherein at least one of the markers is disposed within the housing.

16. The x-ray system of claim 1, wherein at least one of the markers is disposed outside of the housing.

17. An x-ray system, comprising:
means for housing imaging layers;
a plurality of means for generate an image in response to a corresponding incident x-ray beam, disposed in the means for housing imaging layers; and
a plurality of means for affecting the incident x-ray beam for each of the imaging layers.

18. The x-ray system of claim 17, further comprising:
means for moving the means for affecting the incident x-ray beam for each of the imaging layers.

* * * * *